United States Patent
McGillicuddy et al.

(10) Patent No.: US 11,497,480 B2
(45) Date of Patent: Nov. 15, 2022

(54) APPARATUS AND METHODS FOR ASPIRATING TISSUE

(71) Applicant: Cervos Medical LLC, Marshfield, MA (US)

(72) Inventors: Andrew McGillicuddy, Humarock, MA (US); Andy H. Levine, Newton Highlands, MA (US); Neil F. Duffy, Jr., Brighton, MA (US)

(73) Assignee: Cervos Medical LLC, Marshfield, MA (US)

( * ) Notice: Subject to any disclaimer, the term of this patent is extended or adjusted under 35 U.S.C. 154(b) by 641 days.

(21) Appl. No.: 16/277,438

(22) Filed: Feb. 15, 2019

(65) Prior Publication Data

US 2019/0314004 A1 Oct. 17, 2019

Related U.S. Application Data

(62) Division of application No. 14/439,022, filed as application No. PCT/US2013/067358 on Oct. 29, 2013, now Pat. No. 10,231,716.

(Continued)

(51) Int. Cl.
*A61B 10/02* (2006.01)
*A61B 90/00* (2016.01)

(52) U.S. Cl.
CPC ........ *A61B 10/0283* (2013.01); *A61B 10/025* (2013.01); *A61B 2010/0258* (2013.01); *A61B 2090/062* (2016.02); *A61M 2202/10* (2013.01)

(58) Field of Classification Search
CPC .............. A61B 10/0283; A61B 10/025; A61B 2010/0258; A61B 2090/062; A61M 2202/10
See application file for complete search history.

(56) References Cited

U.S. PATENT DOCUMENTS

| 3,893,445 A | 7/1975 | Hofsess |
| 4,010,737 A | 3/1977 | Vilaghy et al. |

(Continued)

FOREIGN PATENT DOCUMENTS

| WO | WO 2006/027549 A1 | 3/2006 |
| WO | WO 2010/138895 A3 | 2/2010 |

(Continued)

OTHER PUBLICATIONS

Al-Ibraheemi et al., "Comparison between 1-needle technique versus 2-needle technique for bone marrow aspiration and biopsy procedures," Arch Pathol Lab Med., 137(7):974-8, Jul. 2013.

(Continued)

*Primary Examiner* — Devin B Henson
(74) *Attorney, Agent, or Firm* — Hamilton, Brook, Smith & Reynolds, P.C.

(57) ABSTRACT

A bone marrow aspiration device and associated method includes an introducer needle and an aspiration needle. The introducer needle includes an introducer cannula and a removable introducer stylet that includes a sharp tip to penetrate bone. The aspiration needle includes an optionally flexible aspiration cannula and a blunt stylet. The aspiration needle is receivable in the introducer cannula when the introducer stylet is removed from the introducer needle. The aspiration cannula forms a channel for aspirating bone marrow when the stylet is removed. The aspiration device also includes a locking mechanism to lock the aspiration cannula to the introducer cannula when the aspiration cannula is received in the introducer cannula, whereby aspiration cannula can be advanced distally relative to the introducer cannula in a controlled manner, and whereby pulling the aspiration cannula proximally causes the introducer cannula to move proximally with the aspiration cannula.

7 Claims, 23 Drawing Sheets

Related U.S. Application Data

(60) Provisional application No. 61/831,383, filed on Jun. 5, 2013, provisional application No. 61/726,913, filed on Nov. 15, 2012, provisional application No. 61/719,611, filed on Oct. 29, 2012.

(56) References Cited

U.S. PATENT DOCUMENTS

| | | |
|---|---|---|
| 4,249,541 A | 2/1981 | Pratt |
| 4,262,676 A | 4/1981 | Jamshidi |
| 4,356,828 A | 11/1982 | Jamshidi |
| 4,366,822 A | 1/1983 | Altshuler |
| 4,469,109 A | 9/1984 | Mehl |
| 4,487,209 A | 12/1984 | Mehl |
| 4,630,616 A | 12/1986 | Tretinyak |
| 4,649,918 A | 3/1987 | Pegg et al. |
| 4,793,363 A | 12/1988 | Ausherman et al. |
| 4,838,282 A | 6/1989 | Strasser et al. |
| 5,026,350 A | 6/1991 | Tanaka et al. |
| 5,027,827 A | 7/1991 | Code et al. |
| 5,279,306 A | 1/1994 | Mehl |
| 5,331,972 A | 7/1994 | Wadhwani et al. |
| 5,357,974 A | 10/1994 | Baldridge |
| 5,368,046 A | 11/1994 | Scarfone et al. |
| 5,429,138 A | 7/1995 | Jamshidi |
| 5,522,398 A | 6/1996 | Goldenberg et al. |
| 5,526,821 A | 6/1996 | Jamshidi |
| 5,807,275 A | 7/1998 | Jamshidi |
| 5,807,276 A | 9/1998 | Russin |
| 5,833,628 A | 11/1998 | Yuan et al. |
| 5,954,671 A | 9/1999 | O'Neill |
| 6,007,496 A | 12/1999 | Brannon |
| 6,063,037 A | 5/2000 | Mittermeier et al. |
| 6,080,115 A | 6/2000 | Rubinstein |
| 6,090,121 A | 7/2000 | Weber et al. |
| 6,110,128 A | 8/2000 | Andelin et al. |
| 6,264,618 B1 | 7/2001 | Landi et al. |
| 6,302,852 B1 | 10/2001 | Fleming et al. |
| 6,312,394 B1 | 11/2001 | Fleming, III |
| 6,416,484 B1 | 7/2002 | Miller et al. |
| 6,425,887 B1 | 7/2002 | McGuckin et al. |
| 6,478,751 B1 | 11/2002 | Krueger et al. |
| 6,554,778 B1 | 4/2003 | Fleming |
| 6,554,803 B1 | 4/2003 | Ashman |
| 6,730,043 B2 | 5/2004 | Krueger et al. |
| 6,755,793 B2 | 6/2004 | Lamoureux et al. |
| 6,849,051 B2 | 2/2005 | Sramek et al. |
| 6,905,489 B2 | 6/2005 | Mantell et al. |
| 6,916,292 B2 | 7/2005 | Morawski et al. |
| 6,981,948 B2 | 1/2006 | Pellegrino et al. |
| 7,081,123 B2 | 7/2006 | Merboth et al. |
| 7,179,232 B2 | 2/2007 | Sutton et al. |
| 7,278,972 B2 | 10/2007 | Lamoureux et al. |
| 7,462,181 B2 | 12/2008 | Kraft et al. |
| 7,637,872 B1 | 12/2009 | Fox |
| 7,850,651 B2 | 12/2010 | Allee et al. |
| 8,043,253 B2 | 10/2011 | Kraft |
| 8,343,133 B2 | 1/2013 | Allee et al. |
| 9,017,298 B2 | 4/2015 | Allee et al. |
| 9,226,732 B2 | 1/2016 | Azimpoor |
| 10,231,716 B2 | 3/2019 | McGillicuddy et al. |
| 10,556,046 B2 | 2/2020 | McGillicuddy |
| 10,568,661 B2 | 2/2020 | McGillicuddy |
| 10,993,707 B2 | 5/2021 | McGillicuddy |
| 11,039,817 B2 | 6/2021 | McGillicuddy |
| 2001/0001811 A1 | 5/2001 | Burney et al. |
| 2003/0050574 A1 | 3/2003 | Krueger |
| 2004/0077973 A1 | 4/2004 | Groenke et al. |
| 2004/0127814 A1 | 7/2004 | Negroni |
| 2004/0153005 A1 | 8/2004 | Krueger |
| 2004/0191897 A1 | 9/2004 | Muschler |
| 2006/0247552 A1 | 11/2006 | Ikehara et al. |
| 2006/0276747 A1 | 12/2006 | Moos et al. |
| 2007/0016100 A1 | 1/2007 | Miller |
| 2007/0055282 A1 | 3/2007 | Muschler |
| 2007/0066987 A1 | 3/2007 | Scanlan, Jr. et al. |
| 2007/0198043 A1 | 8/2007 | Cox et al. |
| 2007/0293788 A1 | 12/2007 | Entrekin et al. |
| 2008/0045857 A1 | 2/2008 | Miller et al. |
| 2008/0214957 A1 | 9/2008 | Verra et al. |
| 2009/0149774 A1 | 6/2009 | Simon et al. |
| 2010/0069843 A1 | 3/2010 | Allee et al. |
| 2010/0280410 A1 | 11/2010 | Moos et al. |
| 2011/0082425 A1 | 4/2011 | Wuestemann. et al. |
| 2011/0112436 A1 | 5/2011 | Jones et al. |
| 2012/0035501 A1 | 2/2012 | Landrigan et al. |
| 2012/0116247 A1 | 5/2012 | Wawrzyniak et al. |
| 2012/0129676 A1 | 5/2012 | Duffy et al. |
| 2012/0136277 A1 | 5/2012 | Landrigan et al. |
| 2013/0131545 A1 | 5/2013 | Azimpoor |
| 2013/0150752 A1 | 6/2013 | Swann |
| 2014/0081318 A1 | 3/2014 | Houser et al. |
| 2016/0106462 A1 | 4/2016 | McGillicudy et al. |
| 2016/0331878 A1 | 11/2016 | McGillicuddy et al. |
| 2018/0085144 A1 | 3/2018 | McGillicuddy |
| 2020/0129680 A1 | 4/2020 | McGillicuddy et al. |
| 2020/0205792 A1 | 7/2020 | McGillicuddy |
| 2020/0305930 A1 | 10/2020 | McGillicuddy |
| 2021/0038201 A1 | 2/2021 | McGillicuddy |
| 2021/0315553 A1 | 10/2021 | McGillicuddy |

FOREIGN PATENT DOCUMENTS

| | | |
|---|---|---|
| WO | WO 2010/138895 A2 | 12/2010 |
| WO | WO 2012/047984 A1 | 4/2012 |
| WO | WO 2013/096419 A1 | 6/2013 |
| WO | WO 2014/070804 A1 | 5/2014 |
| WO | WO 2015/109100 A1 | 7/2015 |

OTHER PUBLICATIONS

Islam, A., "Bone marrow aspiration before bone marrow core biopsy using the same bone marrow biopsy needle: a good or bad practice?," J Clin Pathol., 60(2): 212-215, Feb. 2007.

Bhootra, B.L. "1. Fatality Following a Sternal Bone Marrow Aspiration Procedure," Medicine, Science and the Law. 2004;44(2):170-172. doi:10.1258/rsmmsl.44.2.170, 2004.

Islam, A., "New sternal puncture needle," J. Clin. Pathol., 44, pp. 690-691, 1991.

Malempati et al., "Bone marrow aspiration and biopsy," N. Engl J. Med. 36(15), NEJM.org, 2009.

Definition of offset (Dictionary.com on Jun. 4, 2018).

U.S. Office Action for U.S. Appl. No. 15/110,520, dated Apr. 17, 2019 entitled "Bone Marrow Harvesting Needle Improvements,".

U.S. Non Final Office Action for U.S. Appl. No. 15/110,520, entitled, "Bone Marrow Harvesting Needle Improvements," dated Dec. 17, 2018.

U.S. Office Action for U.S. Appl. No. 14/885,821, dated Apr. 5, 2019 entitled "Bone Marrow Aspiration Device And Method,".

U.S. Final Office Action for U.S. Appl. No. 14/885,821, dated Jun. 14, 2018, entitled "Bone Marrow Aspiration Device And Method," 21 pages.

U.S. Office Action for U.S. Appl. No. 15/721,123, dated Mar. 29, 2019, entitled "Bone Marrow Access Device,".

Hernigou et al., "Percutaneous Autologous Bone-Marrow Grafting for Nonunions. Surgical Technique," The Journal of Bone and Joint Surgery, Inc., vol. 88-A1, Supplement 1, Part 2, Sep. 2006.

Muschler et al., "Aspiration to Obtain Osteoblast Progenitor Cells from Human Bone Marrow: The Influence of Aspiration Volume," The Journal of Bone and Joint Surgery, Inc., vol. 79-A, No. 11, Nov. 1997.

Notice of Allowance and Fees Due, U.S. Appl. No. 15/110,520, entitled "Bone Marrow Harvesting Needle Improvements," dated Oct. 1, 2019.

Notice of Allowance and Fees Due, U.S. Appl. No. 15/721,123, entitled "Bone Marrow Access Device," dated Oct. 4, 2019.

International Search Report and Written Opinion, PCT/US2015/011614, "Bone Marrow Harvesting Needle Improvements," dated Apr. 20, 2015.

(56) References Cited

OTHER PUBLICATIONS

International Search Report and Written Opinion, PCT/US2013/067358, "Apparatus And Methods For Aspirating Tissue," dated Feb. 21, 2014.

International Preliminary Report on Patentability and Written Opinion, PCT/US2013/067358, "Apparatus And Methods For Aspirating Tissue," dated May 5, 2015.

Harrell. D.V., et al., "Novel Technology to Increase Concentrations of Stem and Progenitor Cells in Marrow Aspiration," downloaded from www.marrowcellutions.com on Oct. 7, 2015 (8 pages).

Notification of Transmittal of the International Search Report and the Written Opinion of the International Searching Authority, or the Declaration, "Apparatus And Methods For Aspirating And Separating Components Of Different Densities From A Physiological Fluid Containing Cells", dated Aug. 18, 2011.

Ranfac—Endocellutions, "Legacy Needles are designed to pull a Small Aspirate From a Single Location," downloaded from www.marrowcellutions.com on Oct. 7, 2015 (1 page).

Ranfac—Endocellutions, "Marrow Cellution™—Bone Marrow Harvesting Systems," downloaded from www.marrowcellutions.com on Oct. 7, 2015 (2 pages).

Ranfac—Endocellutions, Presentation, "Marrow Cellution," downloaded from www.marrowcellutions.com on Oct. 7, 2015 (12 pages).

Ranfac, Fact Sheet, "MARROW CELLUTION—Bone Marrow Aspiration and Stem Cell Harvesting Systems," downloaded from www.marrowcellutions.com on Dec. 23, 2015 (2 pages).

Scarpone, M. A. et al., "Marrow Cellution Bone Marrow Aspiration System and Related Concentrations of Stem and Progenitor Cells," downloaded from www.marrowcellutions.com on Dec. 23, 2015 (6 pages).

Snarecoil™ Biopsy Needles—Technology that reduces the TIME and TRAUMA of Bone Marrow Biopsies, retrieved from www.ranfac.com/pdf/bonemarrow.pdf, Mar. 15, 2010, (4 pages).

Notification Concerning Transmittal of International Preliminary Report on Patentability, "Bone Marrow Harvesting Needle Improvements." dated Jul. 28, 2016.

U.S. Office Action for U.S. Appl. No. 14/885,821, entitled "Bone Marrow Aspiration Deice And Method," dated Sep. 11, 2017.

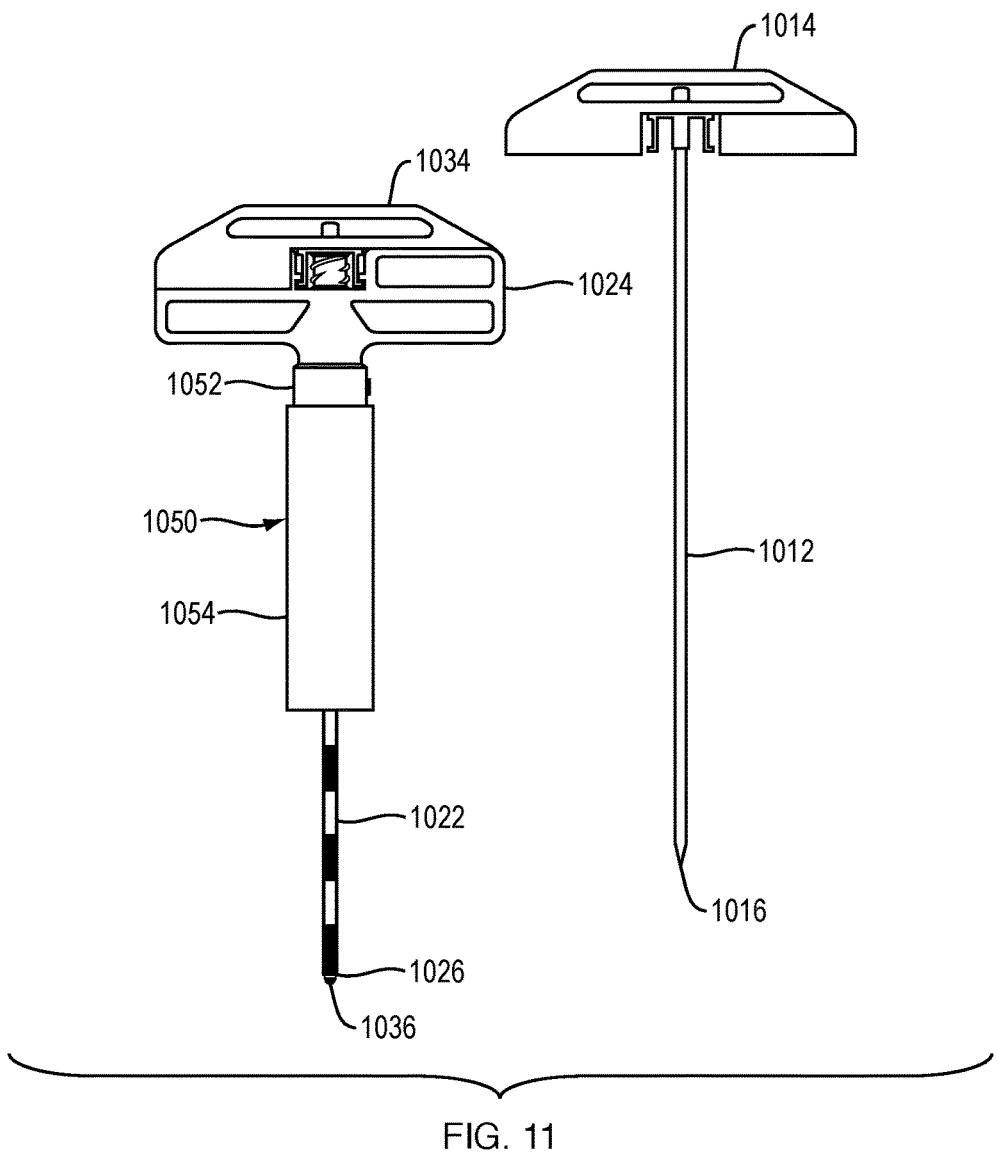
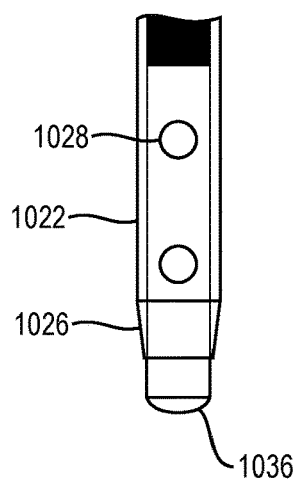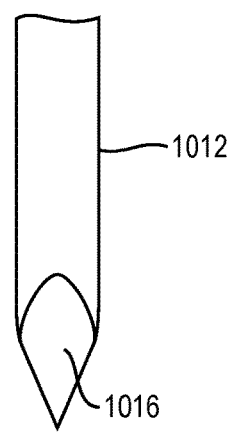
FIG. 11
FIG. 12　　　　　　　FIG. 13

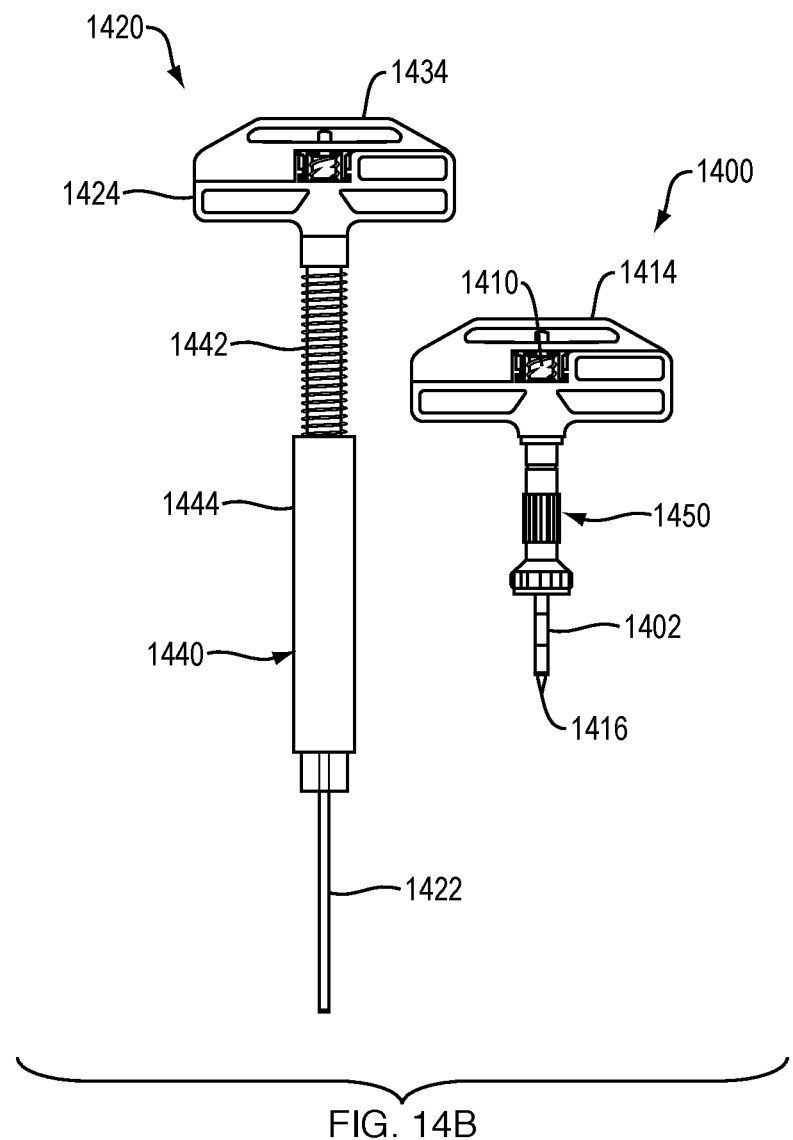

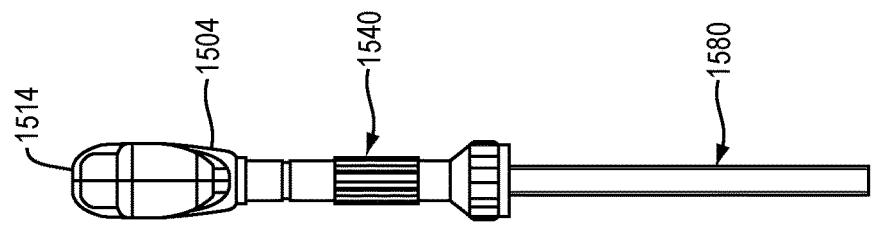
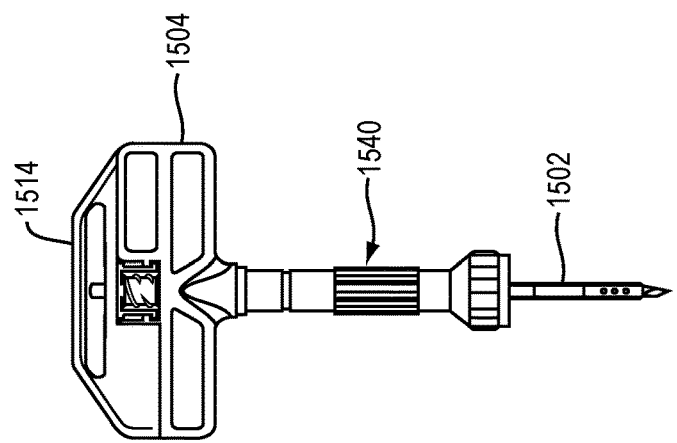
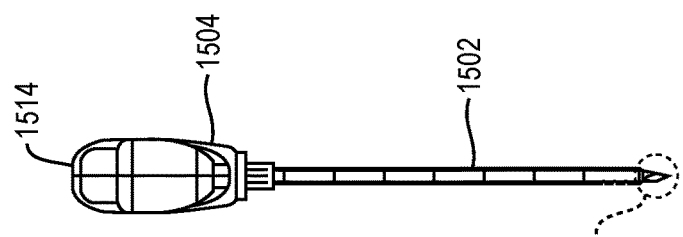
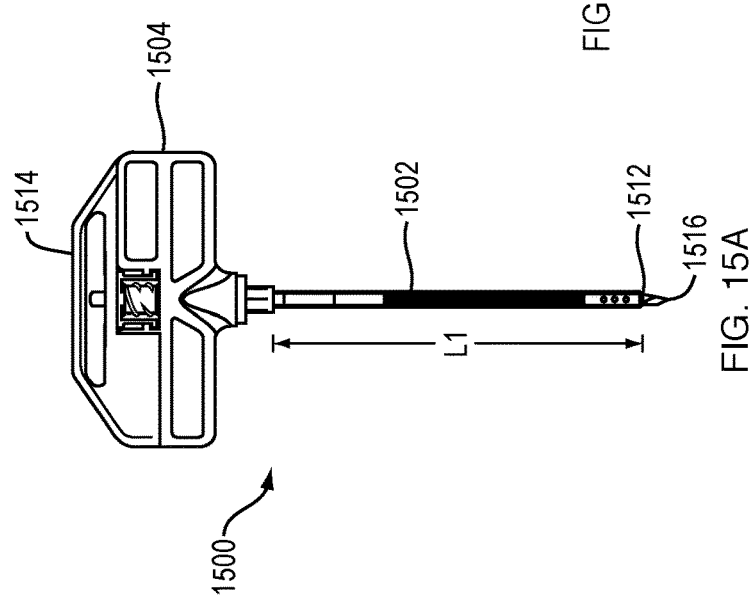
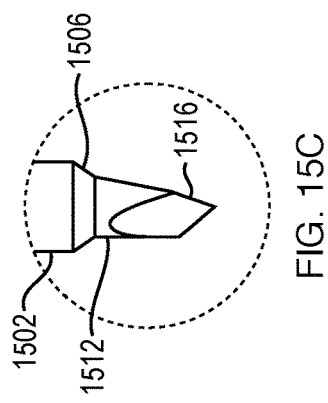

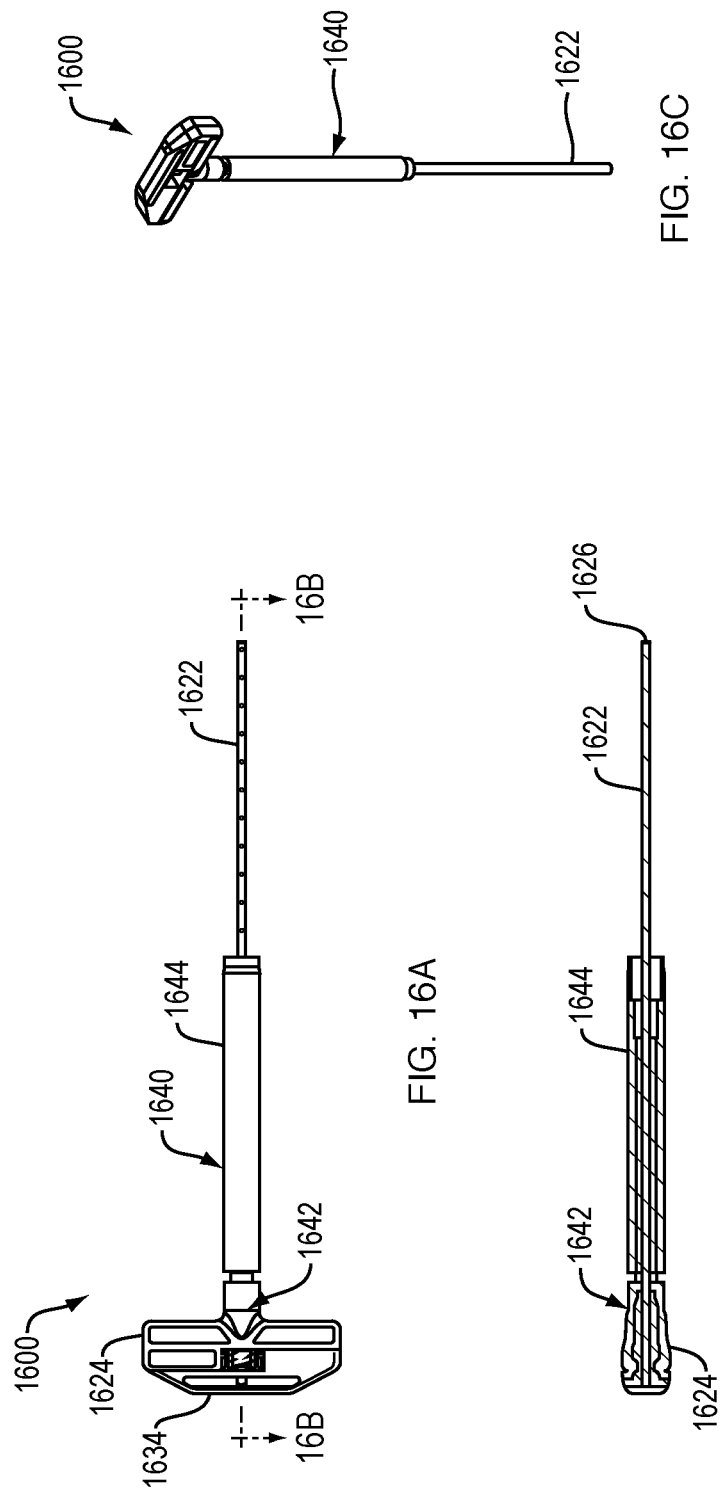

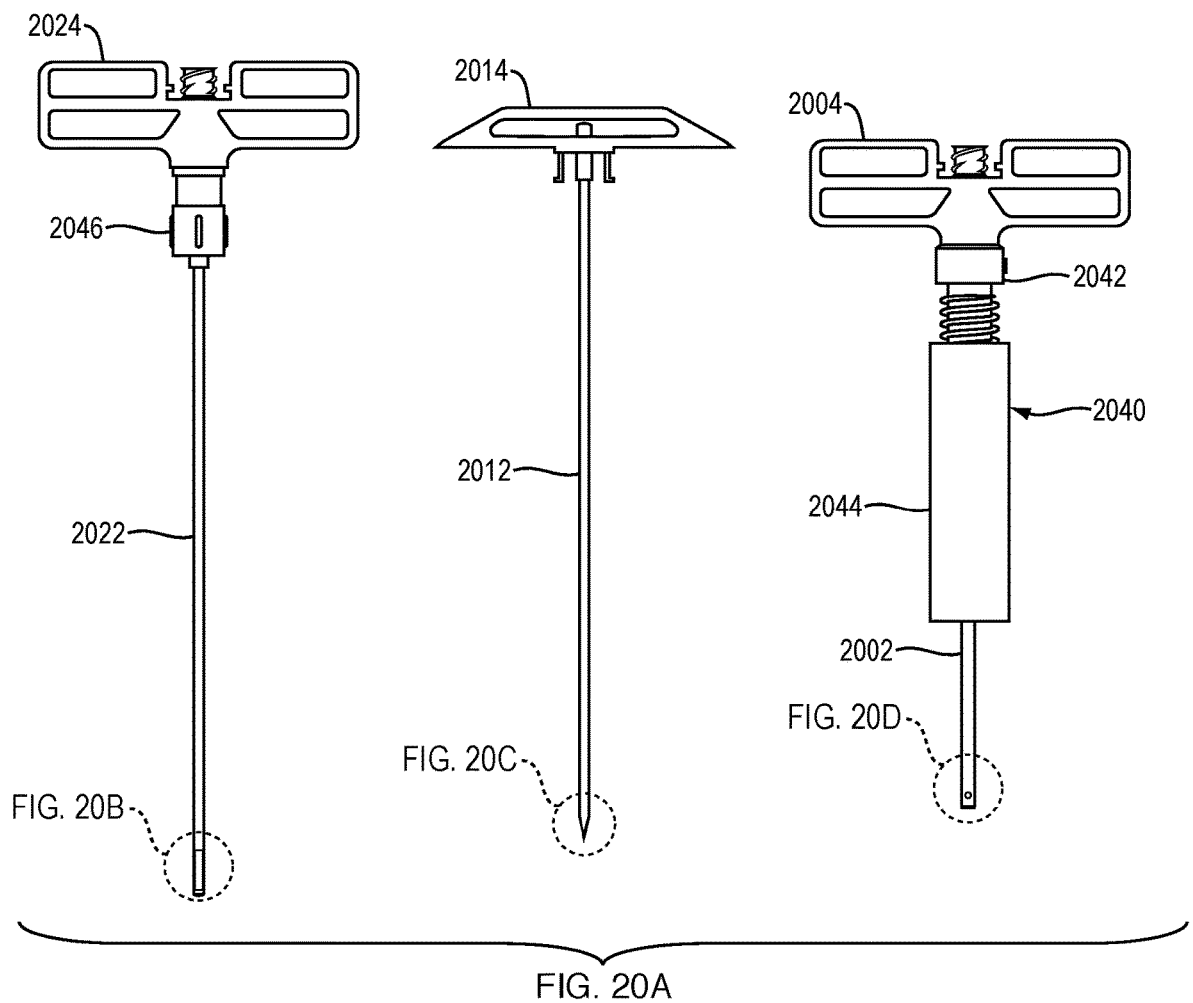
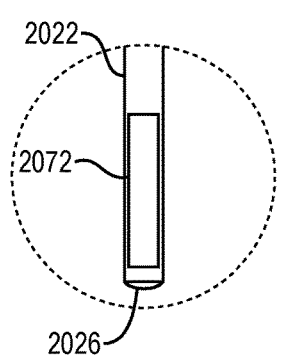
FIG. 20B
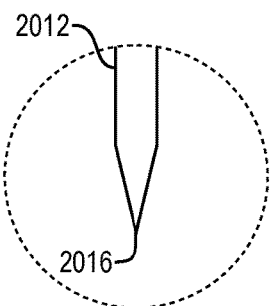
FIG. 20C
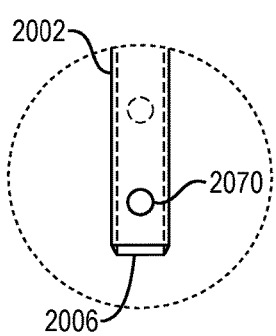
FIG. 20D

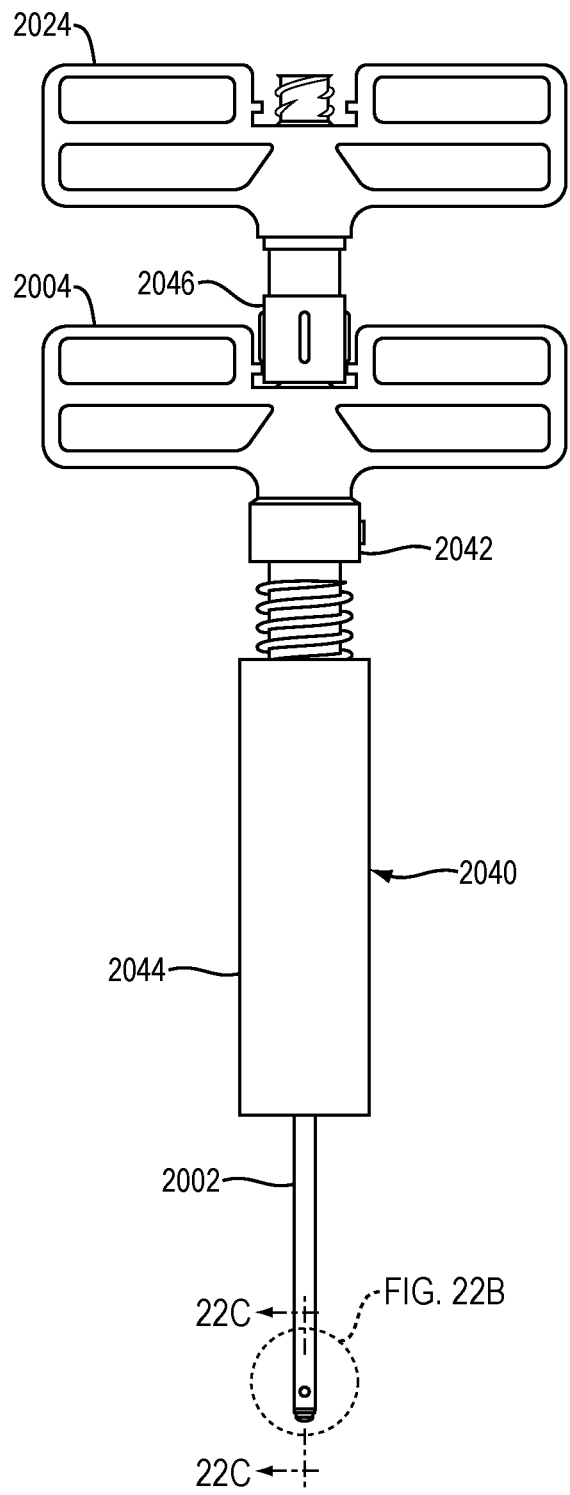
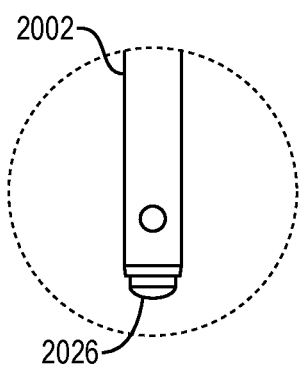
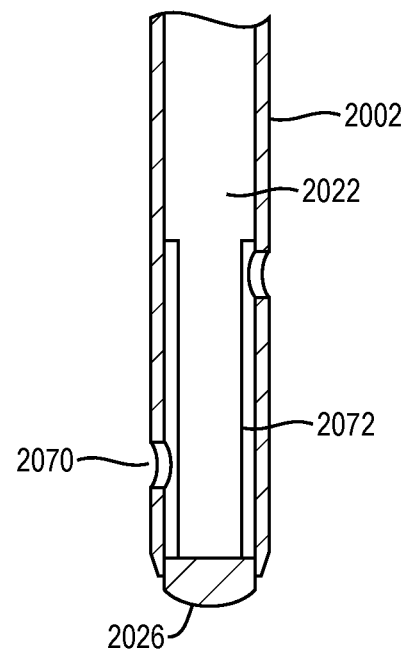
FIG. 22A
FIG. 22B
FIG. 22C

APPARATUS AND METHODS FOR ASPIRATING TISSUE

This application is a divisional of U.S. application Ser. No. 14/439,022, filed on Oct. 29, 2013, which is the U.S. National Stage of International Application No. PCT/US2013/067358, filed on Oct. 29, 2013, which designates the U.S., published in English, and claims the benefit of U.S. Provisional Application No. 61/719,611, filed on Oct. 29, 2012; and U.S. Provisional Application No. 61/726,913, filed on Nov. 15, 2012; and U.S. Provisional Application No. 61/831,383, filed on Jun. 5, 2013. The entire teachings of the above applications are incorporated herein by reference.

BACKGROUND OF THE INVENTION

Bone is made up of a hard outer core, known as cortical bone or cortical plate, and a soft spongy interior known as cancellous bone or trabecular bone, which includes a marrow filling in the porous space within the spongy bone (commonly referred to as bone marrow). The cortical plate is very hard and provides the rigid structure to the skeleton, which allows the skeleton to bear weight. Bone marrow is rich in capillary beds.

Marrow aspiration is usually obtained from the hip bone. Currently, to draw larger volumes of marrow, clinicians usually go into the hip bone through the iliac crest. The goal is to penetrate deep into the spongy bone and then to withdraw small aliquots of marrow as the needle is withdrawn. Traditionally, marrow aspiration is performed with an aspiration needle 100 (FIG. 1). This needle has two basic components: a component comprising a handle 104 with a luer connector 110 for attaching a syringe 106 on one end, and a hollow metal tube or cannula 102 (also referred to as a cannulated trocar) on the other end; and a component (not shown in FIG. 1) comprising a second handle attached to a solid metal rod or stylet with a sharp pointed tip. The stylet of the marrow aspiration needle is removable. When assembled, the second handle fits over the first handle and the stylet fits through the cannula 102, including the luer connector 110 and handle 104, such that the pointed tip of the stylet extends past the distal end of the cannula 102. This entire needle assembly is often referred to as a JAMSHIDI® aspiration needle.

To perform a marrow aspiration, a clinical practitioner uses the fully assembled needle to penetrate cortical bone 112 using the point of the stylet. The clinician uses hand pressure or a mallet to tap the assembled aspiration needle through the bone. The cannula and stylet are usually made of stainless steel or titanium. The assembled aspiration needle is very hard and stiff so that the needle will not bend or buckle when longitudinal force is applied against the proximal handle to allow it to penetrate the cortical bone. Once the hard cortical bone 112 is penetrated, the assembled needle easily advances through the trabecular bone, including spongy marrow, 114. During insertion, the stylet is left in place to prevent the hollow cannula from becoming clogged with debris as the needle is pushed through the spongy marrow. Once the needle assembly is advanced sufficiently into the trabecular bone 114, the stylet, including the stylet handle, is removed to expose the luer connector 110. Luer connector 108 of syringe 106 is attached to the luer connector 110 of the needle and a vacuum created by pulling the syringe plunger will remove the marrow (FIG. 1). Marrow aspirate is pulled through the distal end of the cannula 102 and into the syringe 106 as the needle 100 is slowly removed from the marrow space 114.

A traditional bone marrow aspiration needle is typically used to access marrow from the hip or iliac bone. Because the traditional aspiration needle is stiff, the needle can only advance linearly within the marrow space. Once the needle is through the cortical plate, the cannula only has access to whatever marrow is directly ahead of the cannula tip, but cannot bend or access marrow to the sides of the cannula. Thus, clinicians often need to perform multiple punctures in order to gain larger volumes of aspirate from a more diverse cross section of the marrow space. Since the hip bone is long and thin, once the traditional aspiration needle has penetrated cortical bone, the sharp and stiff instrument has the potential to penetrate through the other side of the cortical bone, resulting in significant trauma. Consequently, it is important for the surgeon to have a proper angle and skilled technique to ensure a safe aspiration. Since the iliac crest curves from the front to the back of the patient, the best angle of entry is from the back. Since the stylet is made of a stiff material, once inside the spongy bone, the needle assembly can only go straight, thus requiring multiple punctures to obtain the required volume of aspirate.

A traditional marrow aspiration needle is meant to access bone marrow from larger cavities and is not ideally suited to drawing marrow from the smaller confines such as the vertebral body of the spine. Because of the sharpness and stiffness of a traditional aspiration needle, using such an instrument in the small curved marrow space of a vertebral body would greatly increase the likelihood of introducing trauma. Less invasive and safer methods to access the marrow tissue of the vertebral body are needed in an effort to support the emerging field of orthobiologics. One fast growing area of this field combines marrow aspirate with synthetic matrix material in order to facilitate instrumented assisted spinal fusion.

Therefore, a need exists for a bone marrow aspiration device that can reduce or minimize the aforementioned problems.

SUMMARY OF THE INVENTION

A bone marrow aspiration device includes an introducer needle, an aspiration needle and a locking mechanism to lock the aspiration cannula to the introducer cannula. The introducer needle includes an introducer cannula having a proximal end and a distal end, each end including an opening, an introducer handle connected to the proximal end of the introducer cannula, and a removable introducer stylet. The introducer stylet has a proximal end and a distal end and extends through the introducer cannula from the cannula handle. The distal end of the introducer stylet extends beyond the distal end of the introducer cannula and includes a sharp tip to penetrate bone. The aspiration needle includes an, optionally flexible, aspiration cannula having a proximal end and a distal end, the distal end including an opening, an aspiration handle connected to the distal end of the aspiration cannula, and a removable blunt stylet. The blunt stylet has a proximal end and a distal end and extends through at least a portion of the aspiration cannula from the aspiration handle. The distal end of the blunt stylet can extend beyond the distal end of the aspiration cannula. The aspiration needle is receivable in the introducer cannula when the introducer stylet is removed from the introducer needle. The aspiration cannula forms a channel for aspirating bone marrow when the blunt stylet is removed. The locking mechanism is configured to lock the aspiration cannula to the introducer cannula when the aspiration cannula is received in the introducer cannula, whereby the aspiration cannula can be advanced distally relative to the introducer cannula in a controlled manner, and whereby pulling the aspiration cannula proximally causes the introducer cannula to move proximally with the aspiration cannula.

The locking mechanism can include a ratchet mechanism, a screw mechanism, or combination thereof.

The ratchet mechanism can include one or more teeth at the introducer needle configured to engage the aspiration cannula. In an embodiment, the ratchet mechanism includes a tube positioned over a proximal portion of the aspiration cannula, the tube including at least one of ratchet teeth to engage the introducer handle and holes to engage with a pin of introducer handle. The ratchet mechanism may include a release button to unlock the aspiration cannula from the introducer cannula. In an embodiment, the ratchet mechanism includes an extension extending distally from the aspiration handle and configured to mate with the introducer handle. The extension and the introducer handle can have respective mating ratchet teeth.

Other ratchet mechanisms are contemplated. For example, a ratchet mechanism can include at least one ribbon ratchet extending between the aspiration handle and the introducer handle. For example, the ribbon ratchet may be fixedly coupled to the aspiration handle and may extend from the aspiration handle through a slot in the introducer handle. In another example, the ribbon ratchet is attached to a locking ring configured to couple the ribbon ratchet to the introducer handle, the ribbon ratchet extending from the locking ring through a slot in the aspiration handle.

The screw mechanism can include a threaded guide in a threaded tube, the guide being attached to the aspiration cannula and the tube configured to couple to the introducer cannula. The tube can be configured to couple to the introducer via a luer connection, the luer connection and screw mechanism providing an air-tight fit. The guide can be hollow and the aspiration cannula can pass through the hollow guide and the tube. The screw mechanism can be configured to advance the aspiration cannula distally when the aspiration handle is turned in one direction and to withdraw the aspiration cannula proximally when the aspiration handle is turned in an opposite direction. In an embodiment, a length of the aspiration cannula that extends beyond the distal end of the introducer cannula is adjustable by advancing the threaded guide into the threaded tube or reversing the threaded guide out of the threaded tube.

In another embodiment, the screw mechanism includes a lead screw in a threaded receptor at the aspiration handle, the lead screw having a proximal end and a distal end, the proximal end including a handle, the distal end receivable in a dead-end receptor at the introducer handle.

The aspiration device can further include a depth guide coupled to the introducer handle, the depth guide configured to control depth of entry of the introducer cannula into bone. In one example, the depth guide is adjustable and includes a lead screw and a threaded tube, whereby a length of the introducer cannula that extends beyond a distal end of the depth guide is adjustable by advancing the lead screw into the threaded tube or reversing the lead screw out of the threaded tube. The lead screw can be attached to the introducer handle. In an embodiment, the lead screw is hollow and the introducer cannula extends through the hollow lead screw. For example, the length of the introducer cannula that extends beyond the distal end of the depth guide can be adjustable between about 1 and about 8 inches.

In some embodiments, the distal end of the aspiration cannula is open, which can be opening near the distal end, for example, in a side of the aspiration cannula. The distal end of the blunt stylet can be configured to extend beyond the distal end of the aspiration cannula. In some embodiments, the distal end of the aspiration cannula is closed and the aspiration cannula includes one or more ports in fluid communication with the channel for aspirating bone marrow. The port(s) can be near the distal end of aspiration cannula. In some embodiments, the aspiration cannula includes plural ports along a length of the aspiration cannula. The ports may vary in size along a length of the aspiration cannula. For example, ports near the proximal end of aspiration cannula can be larger than ports near the distal end of aspiration cannula.

In an embodiment, the aspiration cannula includes a wire wound tube. The entire length of the cannula may be formed of wire wound tube or only a portion thereof. For example, a portion of the aspiration cannula, e.g., a proximal portion, may be a solid wall cannula to which a wire wound portion is welded or attached by other suitable means. The wire wound tube can have a winding in one direction and the locking mechanism can be configured to allow the aspiration cannula to be withdrawn from the bone marrow by turning the aspiration handle in a direction opposite to direction of the winding, whereby the wire wound tube is tightened as the aspiration cannula is withdrawn.

The aspiration cannula can be flexible and the length of the aspiration cannula may be substantially greater than the length of the introducer cannula. In one embodiment, the stiffness of the assembled introducer cannula and stylet is sufficiently high to allow the introducer cannula and stylet to penetrate cortical bone when a longitudinal force is applied to the introducer cannula and stylet in a distal direction. The stiffness of the assembled aspiration cannula and stylet can be sufficiently high to allow the aspiration cannula and stylet to penetrate bone marrow when a longitudinal force is applied to the aspiration cannula and stylet in a distal direction. Further, the stiffness of the assembled aspiration cannula and stylet can be sufficiently low to not allow the aspiration cannula and stylet to penetrate cortical bone but to flex or bend when a longitudinal force is applied to the aspiration cannula and stylet in a distal direction. The introducer cannula may be substantially straight when the introducer stylet extends through the introducer cannula, but may revert to a preset bend when the stylet is removed.

In some embodiments, the introducer cannula includes plural holes. The holes can be near the distal end of the introducer cannula, for example along a side of the introducer cannula. The aspiration cannula can include a cutout alignable with at least one of the plural holes of the introducer cannula. In one example, the distal end of the aspiration cannula is configured to close the opening of the distal end of the introducer cannula. The aspiration needle can include a connector, e.g., a luer connector, to couple to the introducer needle in an air-tight manner.

In an embodiment, a bone marrow aspiration device includes an aspiration needle including a flexible aspiration cannula having a proximal end and a distal end, the proximal end including an opening, an aspiration handle connected to the proximal end of the aspiration cannula, and a removable blunt stylet having a proximal end and a distal end. The stylet extends through at least a portion of the aspiration cannula from the aspiration handle. The aspiration cannula forms a channel for aspirating bone marrow when the blunt stylet is removed. The aspiration device further includes a depth guide coupled to the aspiration handle, the depth guide configured to control depth of entry of the aspiration cannula into bone.

A method for aspirating bone marrow includes inserting an aspiration needle into bone marrow through an introducer cannula placed in a bone, the aspiration needle including an aspiration cannula and a stylet, removing the stylet from the aspiration needle, the aspiration cannula forming a channel for aspirating bone marrow when the stylet is removed, and aspirating bone marrow through the channel. The method further includes locking the aspiration cannula to the introducer cannula with a locking mechanism, whereby the aspiration cannula can be advanced distally relative to the introducer cannula in a controlled manner, and whereby pulling the aspiration cannula proximally causes the introducer cannula to move proximally with the aspiration cannula. The aspiration cannula has a proximal end and a distal end, the proximal end including an opening. The aspiration cannula can be flexible and the length of the aspiration cannula can be substantially greater than the length of the introducer cannula. The aspiration needle further includes an aspiration handle connected to the proximal end of the aspiration cannula. The blunt stylet has a proximal end and a distal end, the stylet extending through at least a portion of the aspiration cannula from the aspiration handle. The distal end of the stylet can extend beyond the distal end of the aspiration cannula.

In an embodiment, inserting the aspiration needle includes flexing or bending the aspiration cannula and stylet against cortical bone. Furthermore, aspirating bone marrow can include retracting the aspiration needle assembly from the bone. The locking mechanism may include a screw mechanism and inserting the aspiration needle can include employing the screw mechanism to advance the aspiration needle distally in a controlled manner. Further, aspirating bone marrow can include retracting the aspiration cannula from the bone, for example, by employing the locking mechanism to move the aspiration cannula proximally with the aspiration cannula. Before the aspiration needle is inserted, the cortical bone may be penetrated with an introducer needle that includes an introducer cannula and a stylet, such as the introducer needle described above, and the introducer stylet may be removed. The method may also include advancing the introducer needle into the bone to a selected depth before removing the introducer stylet.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 11 illustrates the aspiration device of FIG. 10 with the blunt stylet extending through the aspiration cannula.

FIG. 12 is a detailed view of the tapered, distal end of the aspiration cannula and the distal end of the blunt stylet of FIG. 11.

FIG. 13 is a detailed view of the sharp tip of the introducer stylet of FIG. 11.

FIG. 14B illustrates the aspiration needle and introducer needle of FIG. 14A with the blunt stylet inserted into the aspiration cannula and the introducer stylet inserted into the introducer cannula.

FIGS. 15A and 15B are respect front and side views of an example introducer needle.

FIG. 15C is a detailed view of the tip of the introducer stylet of the needle of FIG. 15B.

FIG. 15D is a view of the introducer needle including a depth guide.

FIG. 15E is a side view of the introducer needle of FIG. 15D including a protective sheath.

FIGS. 16A-16C are respective side, sectional and perspective views of an example aspiration cannula including a screw mechanism or depth guard.

FIG. 20A illustrates an aspiration device, including an introducer cannula, introducer stylet, aspiration cannula, and depth guide, according to an example embodiment of the invention.

FIG. 20B is a detailed view of the distal end of the aspiration cannula of FIG. 20A.

FIG. 20C is a detailed view of the distal end of the introducer stylet of FIG. 20A.

FIG. 20D is a detailed view illustrating the distal end of the introducer cannula of FIG. 20A.

FIG. 22A illustrates the assembled aspiration device of FIG. 20A with the aspiration cannula inserted through the introducer cannula.

FIG. 22B is a detailed view of the distal end of the aspiration device of FIG. 22A FIG. 22C is a sectional view of the distal end of the aspiration device of FIG. 22A.

DETAILED DESCRIPTION OF THE INVENTION

A description of example embodiments of the invention follows.

In an improved design, one can access the entire cancellous space with just one puncture. This maximizes the amount of marrow harvested while minimizing the number of punctures needed to place through the bone.

A previously filed patent application (International Application No. PCT/US2010/036696, published on Dec. 2, 2010 as WO2010/138895, incorporated herein by reference in its entirety) addresses limitations of prior bone marrow aspiration needles by introducing through an introducer cannula, a second flexible cannula assembly to access the marrow space. The second cannula is flexible, e.g., made from a polymer, to allow it to curve inside the spongy marrow to access a broader cross section of the marrow space.

An aspiration apparatus is provided that allows for different lengths of needle assemblies to fit coaxially together by removing the trocar or stylet of the previous needle assembly. The outer diameter of the cannula of each successive needle assembly is smaller and the length is longer than the inner diameter and length, respectively, of the cannula of the previous needle assembly. Beyond diameter and length, each successive needle assembly can have other characteristics such as flex and sharpness. Many different diameters, lengths, and stiffness can be incorporated into the design and the design can incorporate two or more needle assemblies in order to make apparatus designed for certain applications. For example, assemblies designed for use in tendon and ligament repair may be different in length, stiffness, or some other material property, such as lubricity, than those designed to be used in osteonecrosis. Assemblies designed to be used in pediatrics may be different in size than those used in an adult, to accommodate a smaller patient, but may also differ in stiffness to reflect potential differences in developing tissue as compared to adult tissue.

Figure 1:
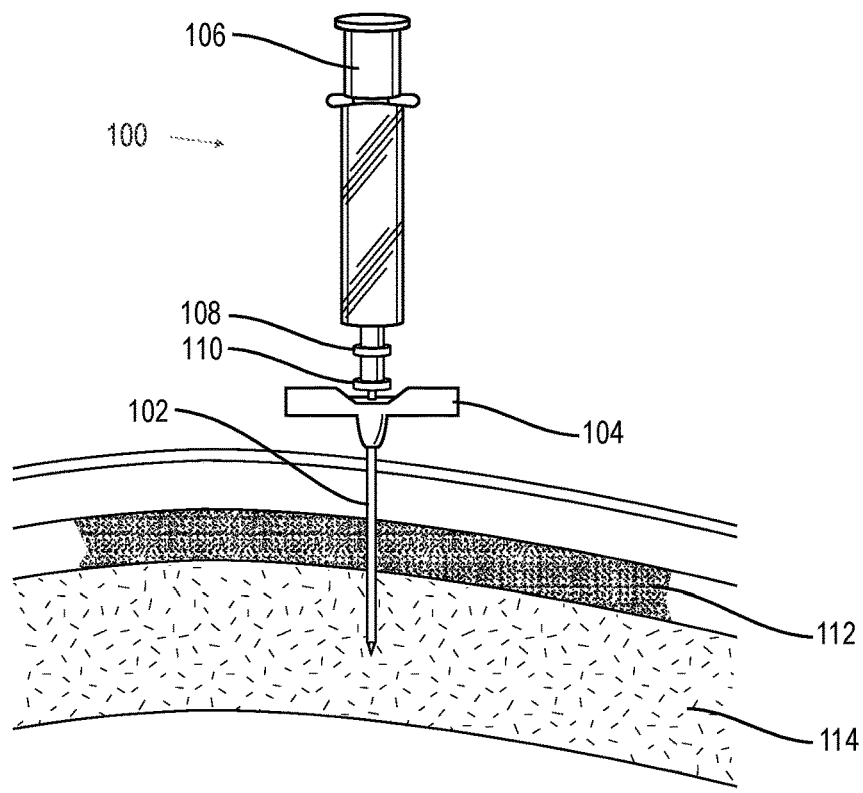
FIG. 1 illustrates bone marrow aspiration with a standard aspiration needle.
Figure 2:
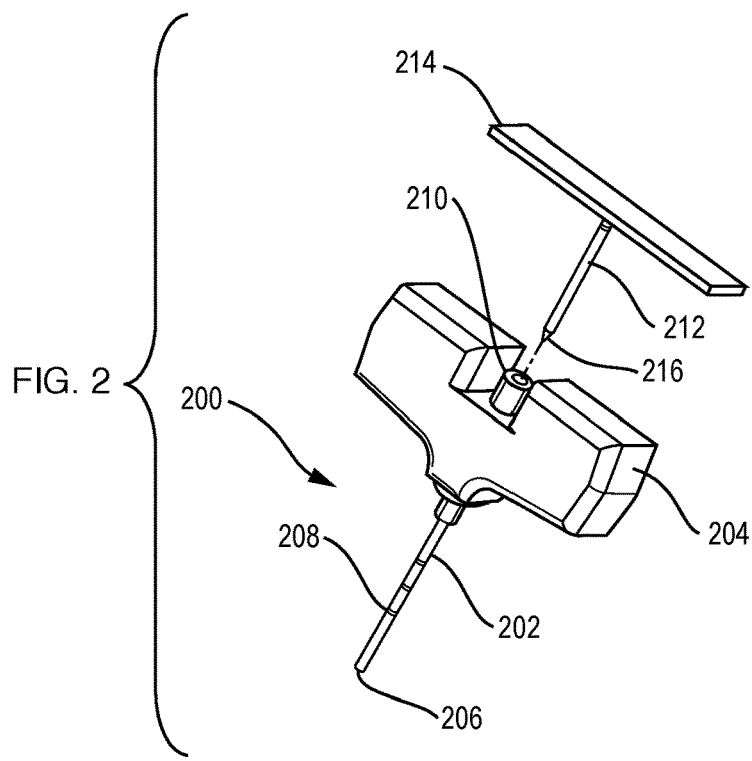
FIG. 2 is a perspective view of an embodiment of an introducer needle assembly showing the introducer stylet removed from the introducer cannula.

As shown in FIG. 2, an introducer needle assembly 200 includes an introducer cannula 202 having a proximal end 206 and a distal end 210, each end including an opening, an introducer handle 204 connected to the proximal end of the introducer cannula, and a removable trocar 212. The trocar 212 has a proximal end and a distal end and fits into the introducer cannula 202. When inserted into the introducer cannula 202, the trocar 212 extends through the introducer cannula 202 from the cannula handle 204. The distal end of the trocar extends beyond the distal end of the introducer cannula and includes a sharp tip 216 to penetrate bone. The trocar may include a trocar handle 214 connected to the proximal end of the trocar. The introducer needle assembly 200 can include a luer connector at the distal end 210 of the cannula to which a syringe or other receptacle can be attached.

Figure 3:
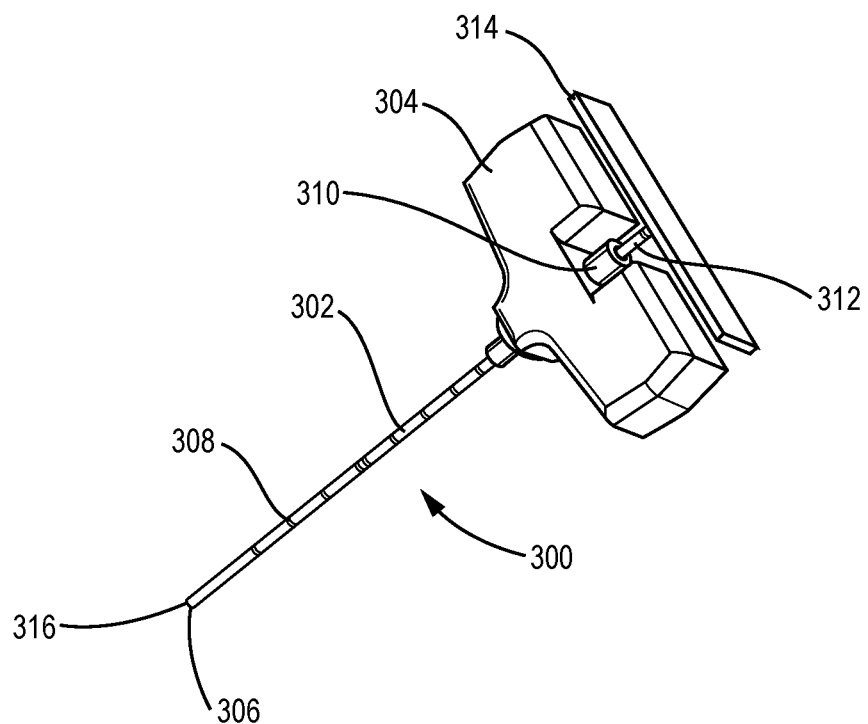
FIG. 3 is a perspective view of an embodiment of a flexible aspiration needle assembly.

As shown in FIG. 3, an aspiration needle assembly 300 includes a flexible aspiration cannula 302 having a proximal end 310 and a distal end 306, each end including an opening, an aspiration handle 304 connected to the distal end 310 of the aspiration cannula, and a flexible stylet 312. The length of the aspiration cannula 302 is substantially greater than the length of the introducer cannula 202 (FIG. 2). The stylet 312 has a proximal end and a distal end and extends through the aspiration cannula 302 from the aspiration handle 304, the distal end of the stylet extending beyond the distal end 306 of the aspiration cannula 302. The aspiration needle assembly 300 is receivable in the introducer cannula 202 when the trocar 212 is removed from the introducer needle assembly 200.

Figure 4:
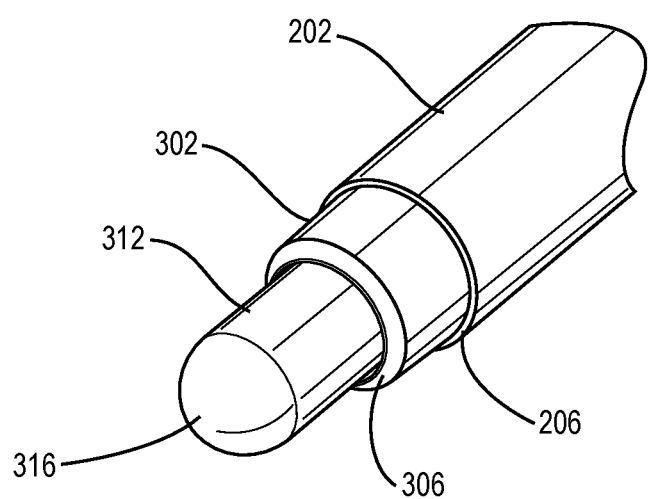
FIG. 4 is a perspective view of the distal end of the aspiration needle assembly of FIG. 3 extending through the distal end of the introducer cannula of FIG. 2.

FIG. 4 is a close-up view showing the distal end 306 of the aspiration cannula 302 and the distal end of the stylet 312 coming out of and extending past the distal end 206 of the introducer cannula 202. The distal end of stylet 312 can include an atraumatic tip 316, such as a round or blunt tip. When fully inserted though introducer cannula 202, the stylet 312 and flexible cannula 302 will extend farther past the distal end 206 than shown in FIG. 5. This is so because of the length of the aspiration cannula 302 is substantially greater than the length of the introducer cannula 202.

Figure 5:
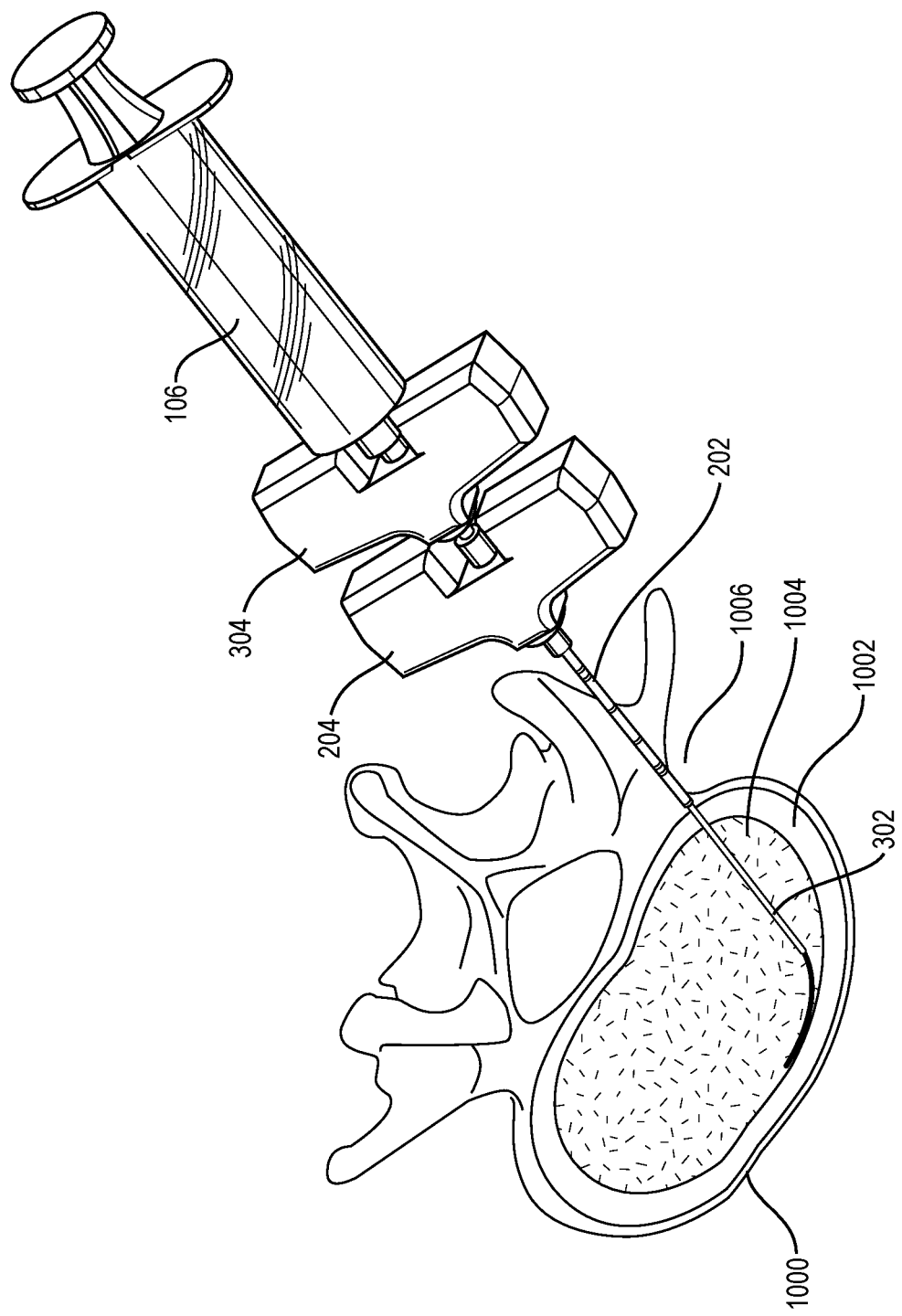
FIG. 5 is a perspective view of an embodiment of an aspiration device inserted into a vertebral body.

FIG. 5 is a perspective view of an embodiment of the aspiration device inserted into a vertebral body. A vertebral body is shown here but the devices described herein can be used for access to other bones, such as the iliac bone, which is more commonly used as a source of bone marrow. As shown, introducer needle assembly 200 has penetrated pedicle 1006 and cortical bone 1002 of vertebral body 1000. Trocar 202 has been removed, leaving introducer cannula 202 in place. Aspiration cannula 302 extends through the introducer cannula 202 and into bone marrow 1004. The stylet 312 has been removed from the aspiration needle assembly 300. With the stylet 312 removed, the aspiration cannula 302 forms a channel for aspirating fluid tissue, including bone marrow. A syringe 106 is connected to the luer connector at the proximal end 310 of the aspiration cannula 302. The distal end 306 of the aspiration cannula 302 substantially extends beyond the distal end 206 of the introducer cannula 202. The distal end 306 of the aspiration cannula is placed in bone marrow and a fluid path exists from the marrow through the aspiration cannula 302 into the syringe 106. The flexible aspiration assembly travels straight through the bone marrow 1004 until deflecting off the cortical bone 1002 opposite the point of entry into the vertebral body 1000. Upon hitting the cortical bone 1002, the aspiration cannula bends and travels along the inside of cortical bone 1002. Since the material of the aspiration needle assembly does not take a permanent shape, both the flexible stylet and aspiration cannula can be easily removed to perform the aspiration.

Figure 6A:
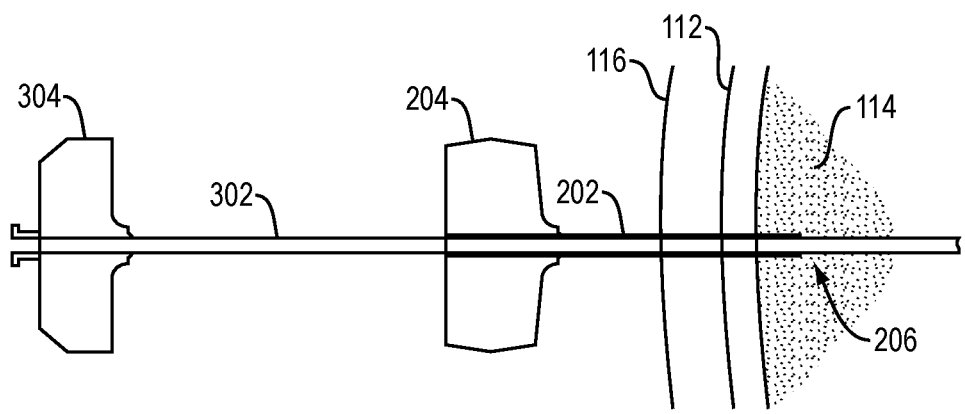
FIG. 6A is a diagram illustrating an aspiration cannula inserted into bone through an introducer cannula.

The introduction of a flexible aspiration cannula however introduces a new problem. FIG. 6A is a diagram illustrating a flexible aspiration cannula 302 inserted through skin 116 into bone (cortical bone 112, bone marrow 114) through an introducer cannula 202. The flexible cannula bends inside the marrow space 114 as designed and does permit access to more of the marrow. However, as marrow is being drawn through the flexible cannula, the cannula is typically pulled back out of the bone so as to suction the marrow in different locations. When this is done, the bent flexible cannula 302 can catch on the sharp leading edge 206 of the introducer cannula 202. This can lock up the cannulae or lead to skiving of the flexible aspiration cannula 302, potentially leaving pieces of the cannula in the patient.

To avoid this interference of introducer cannula with the flexible cannula, embodiments of the invention include features to lock the flexible aspiration cannula to the rigid introducer cannula as the aspiration cannula is introduced through the introducer cannula. As described below, embodiments can include a locking mechanism, such as a ratchet-like mechanism, a lead screw mechanism, or a combination thereof. In this way, the flexible cannula may be pushed into the bone marrow through the introducer cannula. When pulled back out of the bone, the flexible aspiration cannula and the rigid introducer cannula are locked together and will therefore retract together. Since the assembly is retracted, e.g., pulled back, together, the flexible aspiration cannula cannot skive on the rigid cannula, yet the marrow can be suctioned from the cancellous bone as the aspiration cannula is retracted. Since the length of aspiration cannula that is introduced into the bone marrow space is variable, embodiment of the invention include a locking mechanism, e.g., a screw mechanism or ratchet at the handles of the two cannulae, which can accommodate differences in penetration length of the flexible cannula.

Various ratcheting mechanisms between the inner cannula, i.e., aspiration cannula and the outer cannula, i.e., introducer cannula, are described such that the aspiration cannula may enter the bone marrow, but when pulled out, both cannulae travel together.

Figure 6B:
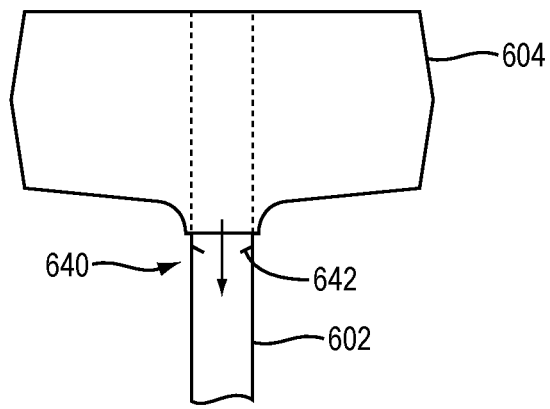
FIGS. 6B and 6C are respective side and sectional views of an introducer needle including a locking mechanism.
Figure 6C:
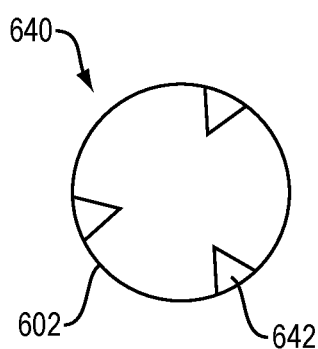

FIGS. 6B and 6C are respective side and sectional views of an introducer needle 602 including a locking mechanism 640. The flexible aspiration cannula, such as cannula 302 of FIG. 6A, can be made of a polymer, preferably polyimide, which can be quite strong and tough. One or more metal teeth 642 are located at the introducer cannula 602, e.g., near the introducer handle 604. As shown, the teeth are extending into an inside of the cannula 602, where the aspiration cannula is received, and are biased in the distal direction (as indicated by the arrow in FIG. 6B), so that the flexible aspiration cannula can advance but when pulled back, the teeth 642 dig into the aspiration cannula to prevent movement in a proximal direction relative to the insertion cannula 602. The teeth 642 and the aspiration cannula 302 function as a ratchet mechanism. When the flexible aspiration cannula is pulled out, the introducer cannula will pull with it.

Figure 7A:
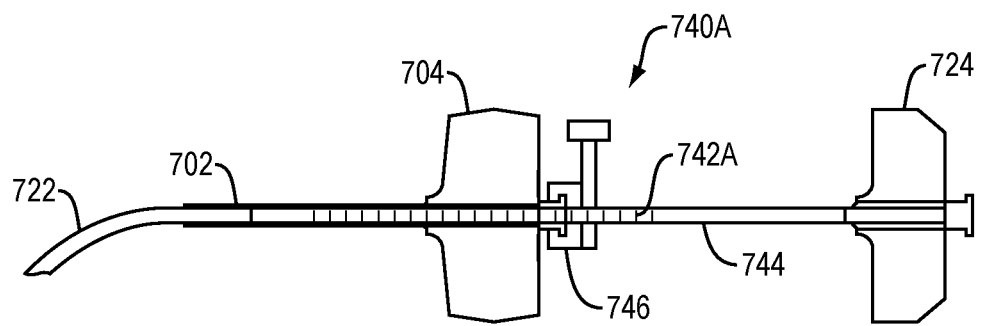
FIG. 7A is a diagram illustrating of an example locking mechanism that includes a ratchet.

FIG. 7A is a diagram illustrating of an example locking mechanism 740A that includes a ratchet 742A. In this embodiment, rather than using the flexible aspiration cannula itself as a ratchet, such as illustrated in FIG. 6B, a hypodermic tube 744 is placed over the proximal portion of the aspiration cannula 722. The hypo tube 744, which need not be flexible, is more robust than the aspiration cannula. Either teeth or holes may be cut into the hypo tube 744 to permit engagement with a pin at the handle 704 of introducer cannula 702. The pin may be part of an adaptor 746 that mounts to introducer handle 704.

Figure 7B:
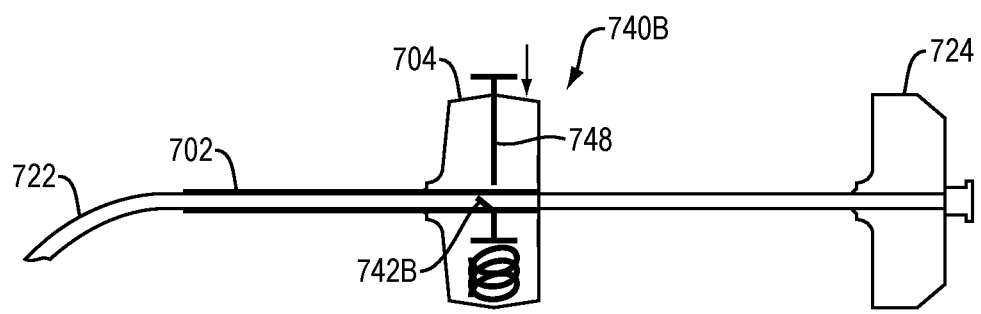
FIG. 7B is a diagram illustrating another example locking mechanism that includes a ratchet.

FIG. 7B is a diagram illustrating another example locking mechanism 740B that includes a ratchet mechanism 742B, including a spring loaded pin. As shown A release button 748 may be provided to separate the aspiration cannula 722 from the introducer cannula 702 once the cannulae are removed from the body for re-use.

Figure 8:
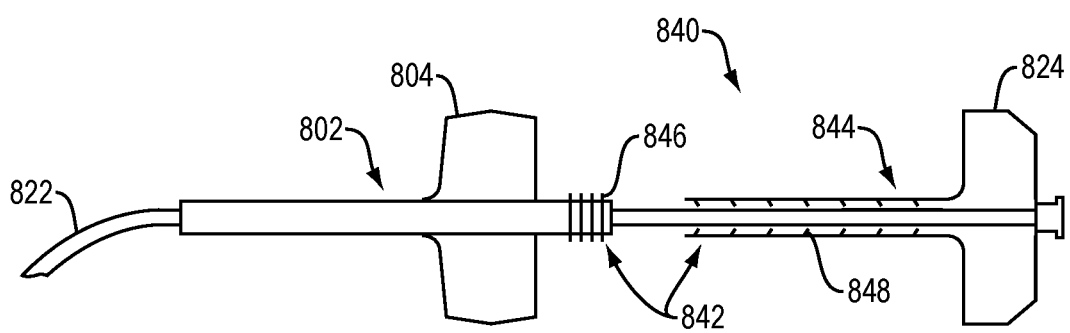
FIG. 8 is a diagram of yet another example locking mechanism that includes a ratchet.

FIG. 8 is a diagram of yet another example locking mechanism 840 that includes a ratchet 842 to lock an aspiration cannula 822 to an introducer cannula 802. In this embodiment, the ratchet mechanism 842 includes an extension 844 that extends distally from the aspiration handle 824 and that is configured to mate with the introducer handle 804. The extension 844 and the introducer handle 802 have respective mating ratchet teeth 846, 848. When the aspiration cannula 822 is advanced into the introducer cannula 802, the extension 844 locks to the introducer handle 804.

Figure 9A:
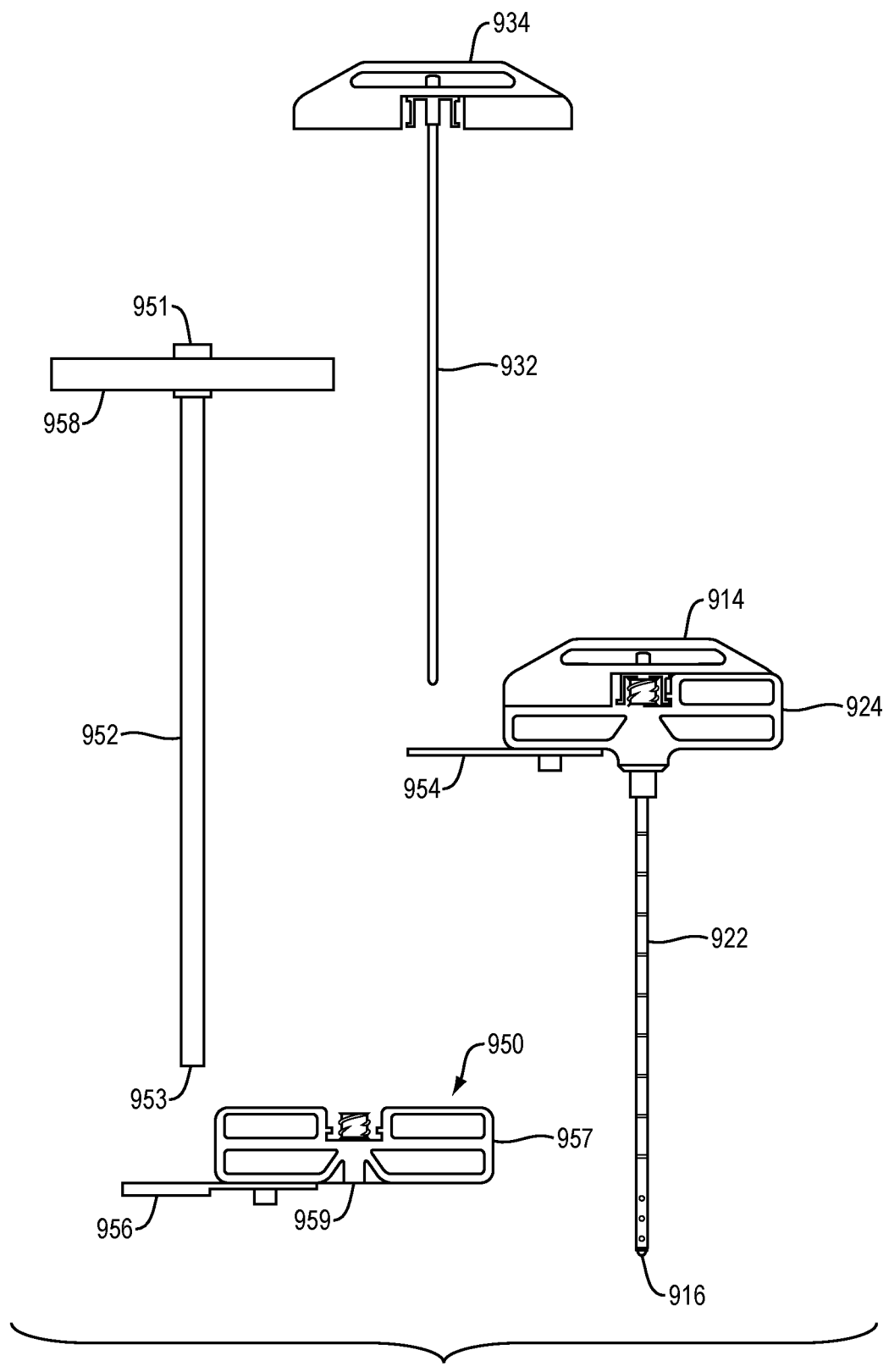
FIG. 9A illustrates an example aspiration device including an aspiration needle and a depth guide including a screw mechanism.
Figure 9B:
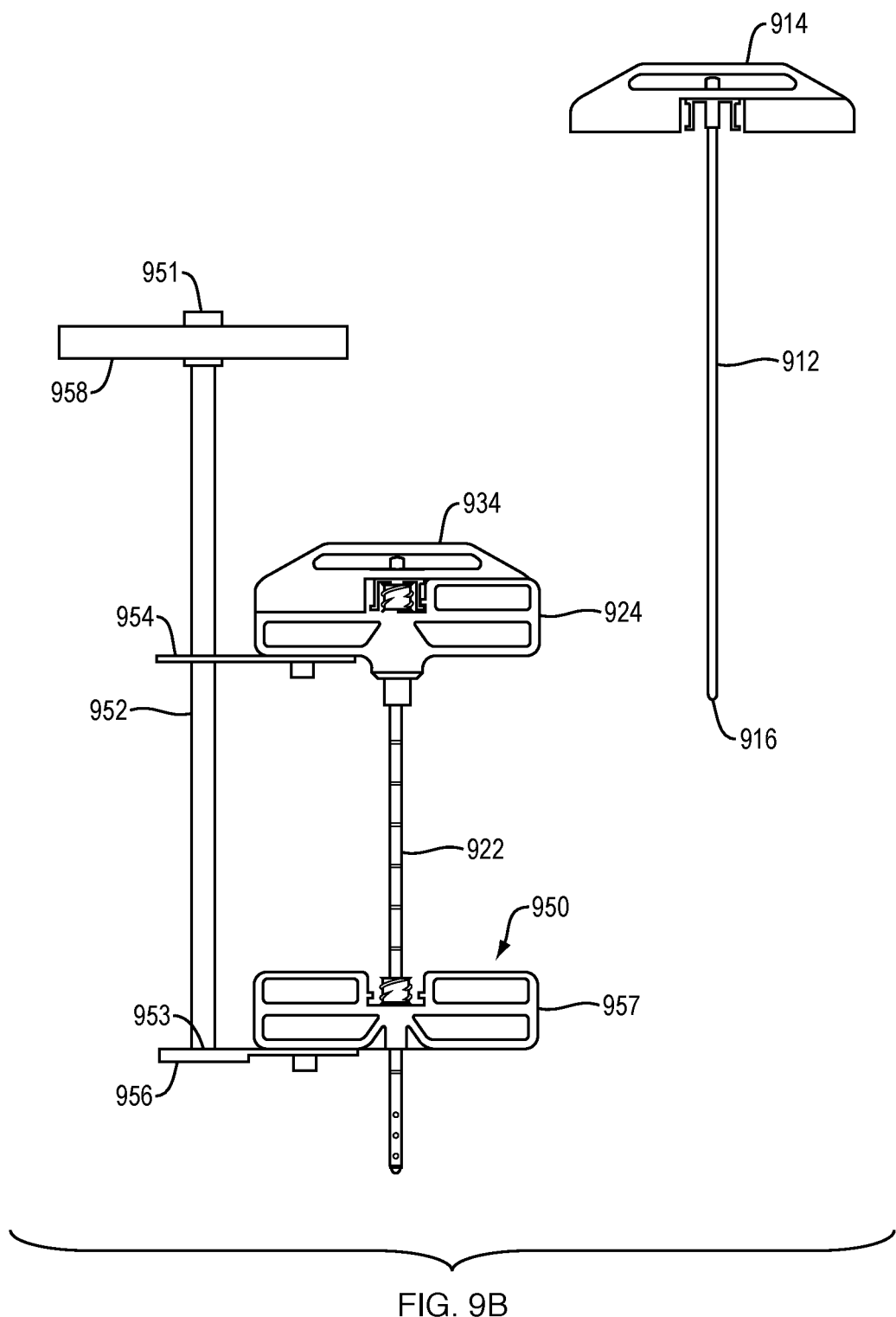
FIG. 9B illustrates the aspiration device of FIG. 9B in a partially assembled state.

FIGS. 9A-9B illustrate an example aspiration device including an aspiration needle, including aspiration cannula 922, blunt stylet 924, and introducer stylet 912. The aspiration cannula 922 can be made of flexible material, such as Nitinol or PEEK, as elsewhere described herein. The introducer stylet 912 includes handle 914. Stylet 912 can be made of steel, lending it sufficient stiffness to penetrate cortical bone, and typical includes a sharp tip at its distal end 916. The blunt stylet 924 includes a handle 934 and can be made of flexible material, e.g., plastic or Nitinol, as described herein. FIG. 9A shows the introducer stylet 912 extending through the aspiration cannula 922. The aspiration device also includes a depth guide 950 including a screw mechanism. In this embodiment, the screw mechanism includes a lead screw 952 receivable in a threaded receptor 954 at the aspiration handle 924. The lead screw 952 has a proximal end 951 and a distal end 953, the proximal end including a handle 958. The distal end 953 is receivable in a dead-end receptor 956 of the depth guide 950.

FIG. 9B illustrates the aspiration device of FIG. 9B in an assembled state with the introducer stylet 912 removed. The lead screw is configured to turn in place in the dead-end receptor 956. By turning the lead screw handle 958, a user can cause the handle 924 of the aspiration cannula 922 to advance down the lead screw, thereby advancing the aspiration cannula into the marrow space. As shown, the depth guide 950 can include a handle 957 which includes a through-hole 959 for receiving the cannula 922. The handle 957 can be a snap-on handle that snaps on to the cannula 922. The handle 957 may be flatter as illustrated in FIGS. 9A-9B, and may be broad, so as to spread force out against the patient (e.g., when a clinician firmly presses the handle against the patent to advance the cannula 922). A flat handle also reduces the possibility of interferences with the aspiration handle 924 as the aspiration cannula advances into bone.

Figure 10:
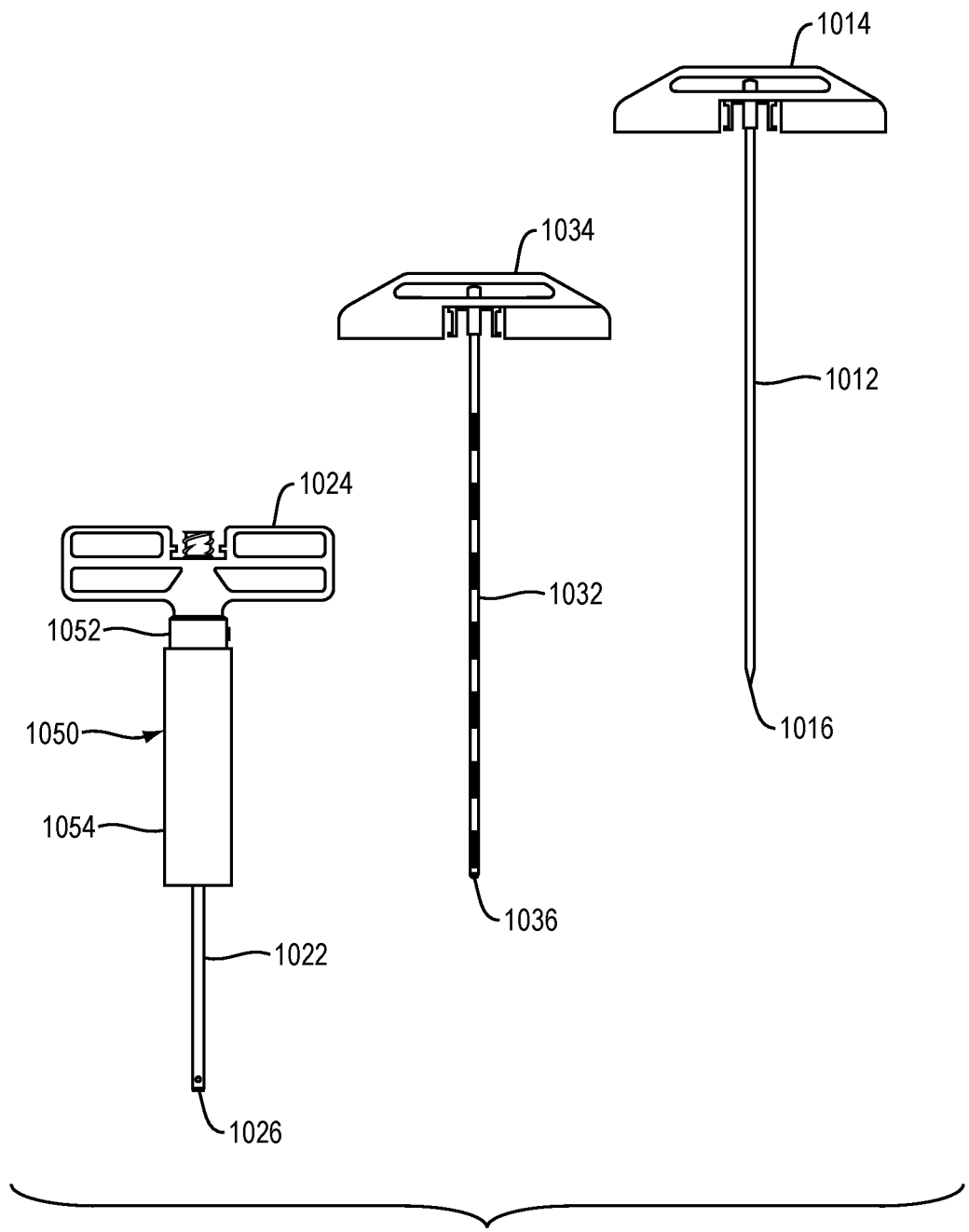
FIG. 10 illustrates an example aspiration device including a flexible aspiration cannula, a blunt stylet, a sharp introducer stylet, and a depth guide.

FIG. 10 illustrates an example aspiration device including a flexible aspiration cannula 1022, a blunt stylet 1032, a sharp introducer stylet 1012, and a depth guide 1050. The depth guide is adjustable and coupled to the aspiration handle 1024 that is attached to a proximal end of the aspiration cannula 1022. The depth guide 1050 is configured to control depth of entry of the aspiration cannula 1022 into bone, e.g., bone marrow.

FIG. 11 illustrates the aspiration device of FIG. 10 with the blunt stylet 1032 extending through the aspiration cannula 1022. The distal end 1036 of the blunt stylet extends past the distal end 1026 of the aspiration cannula. As shown, the depth guide 1050 includes a lead screw 1052 and a threaded tube 1054. A length of the introducer cannula that extends beyond a distal end of the depth guide 1050 is adjustable by advancing the lead screw 1052 into the threaded tube 1054 or reversing the lead screw out of the threaded tube. The lead screw 1052 can be attached to the introducer handle 1024, as shown. As shown, the lead screw 1052 is hollow and the introducer cannula 1022 extends through the hollow lead screw.

FIG. 12 is a detailed view of the tapered, distal end 1026 of the aspiration cannula 1022, and the distal end 1036 of the blunt stylet 1032 of FIG. 11. The aspiration cannula includes multiple holes 1028 along a length of the cannula near the distal end 1026. Bone marrow can be aspirated through holes 1028 and through open distal end 1026, once the blunt stylet 1032 is removed. The aspiration cannula can be flexible or include a flexible portion. As described herein, suitable materials for a flexible aspiration cannula include PEEK, Nitinol, or other materials. FIG. 13 is a detailed view of the sharp tip at the distal end 1016 of the introducer stylet 1012 of FIG. 11.

The depth guides described herein, such as depth guide 1050 of FIGS. 10-11, which includes a screw mechanism, can serve multiple purposes. The depth guide can act as a safety stop when using a mallet for advancing the aspiration needle and can provide leverage for advancement. Further, the depth guide can provide for controlled aspiration during retrieval of the aspiration cannula from the bone marrow.

It will be understood, that devices and methods for aspirating tissue described herein may include other ratcheting mechanisms, screw mechanisms, or combinations thereof, to advance a flexible cannula or needle into patient (e.g., into the marrow space) and/or to lock the flexible needle to an introducer needle (trocar) for withdrawal of the flexible cannula from the patient, e.g., during aspiration of bone marrow.

For example, one or more ribbon ratchets can be attached to the flexible aspiration needle handle. The ribbon(s) can be similar to a tie wrap in that each ribbon has teeth to permit unidirectional movement. One or more mating slots in the introducer needle handle accept the ribbon(s). As the flexible aspiration needle is advanced, the ribbon ratchets forward. When a user pulls back (distally) on the flexible aspiration needle handle, the introducer cannula moves comes back with the aspiration cannula. In another example, the ribbon can be reversed such that the ribbon(s) pass through the flexible aspiration cannula handle. For example, the ribbon ratchet(s) can be pre-attached to the aspiration handle and include a locking ring. When the aspiration cannula is advanced through the introducer cannula, the locking ring locks the ribbon(s) to the introducer cannula handle.

In one embodiment, the screw mechanism includes a lead screw in a threaded receptor at the aspiration handle, the lead screw having a proximal end and a distal end, the proximal end including a handle, the distal end receivable in a dead-end receptor at the introducer handle.

Some embodiments include two aspiration needles (also referred to herein as double needle design(s)), a flexible needle or cannula (inner needle) that is inserted through a stiff introducer needle or trocar (outer needle). The flexible needle can be advanced, for example, into bone marrow space, through the stiff needle to a variable distance using a ratchet or screw mechanism. Both needles can be locked together and pulled out together, e.g., pulled out of the bone marrow space. Aspiration of tissue, e.g., bone marrow, is through the flexible needle (inner needle) and preferably while the needles are being pulled out.

Some embodiments include one aspiration needle (also referred to herein as single needle design(s)), which preferably is a flexible needle or cannula. The flexible needle can be advanced, for example, into bone marrow space, to a variable distance using a ratchet or screw mechanism. The flexible needle is advanced relative to a plate or handle that is positioned against body of the patient, the flexible needle being advanced through a hole in the plate or handle. The plate or handle may be pre-assembled with the flexible needle and can couple, for example, to the handle of the flexible needle via a snap-on fit.

Described herein are improvements to the double needle device to harvest bone marrow previously described in International Application No. PCT/US2010/036696. The previously described aspiration device included a stiff sharp first needle that is used to penetrate the hard outer bone (cortical bone) and a second blunt, flexible needle is used to travel through the spongy trabecular bone. Hand force would be used to advance the second flexible aspiration needle through the cannula of the first needle and into the trabecular bone space. Upon testing, it was observed that while the trabecular bone is not as hard as the cortical bone, it can still be too hard to allow advancement of the aspiration needle by hand. In fact, a hammer may often be required to drive the second needle through the trabecular bone space. Hammering the aspiration needle can lead to problems such as the needle becoming lodged (stuck) inside the bone, or advancing too far, through the back side of the cortical bone potentially hitting soft tissue. An improved aspiration system is described below that allows the second, flexible needle to advance through the trabecular bone without hammering.

Figure 14A:
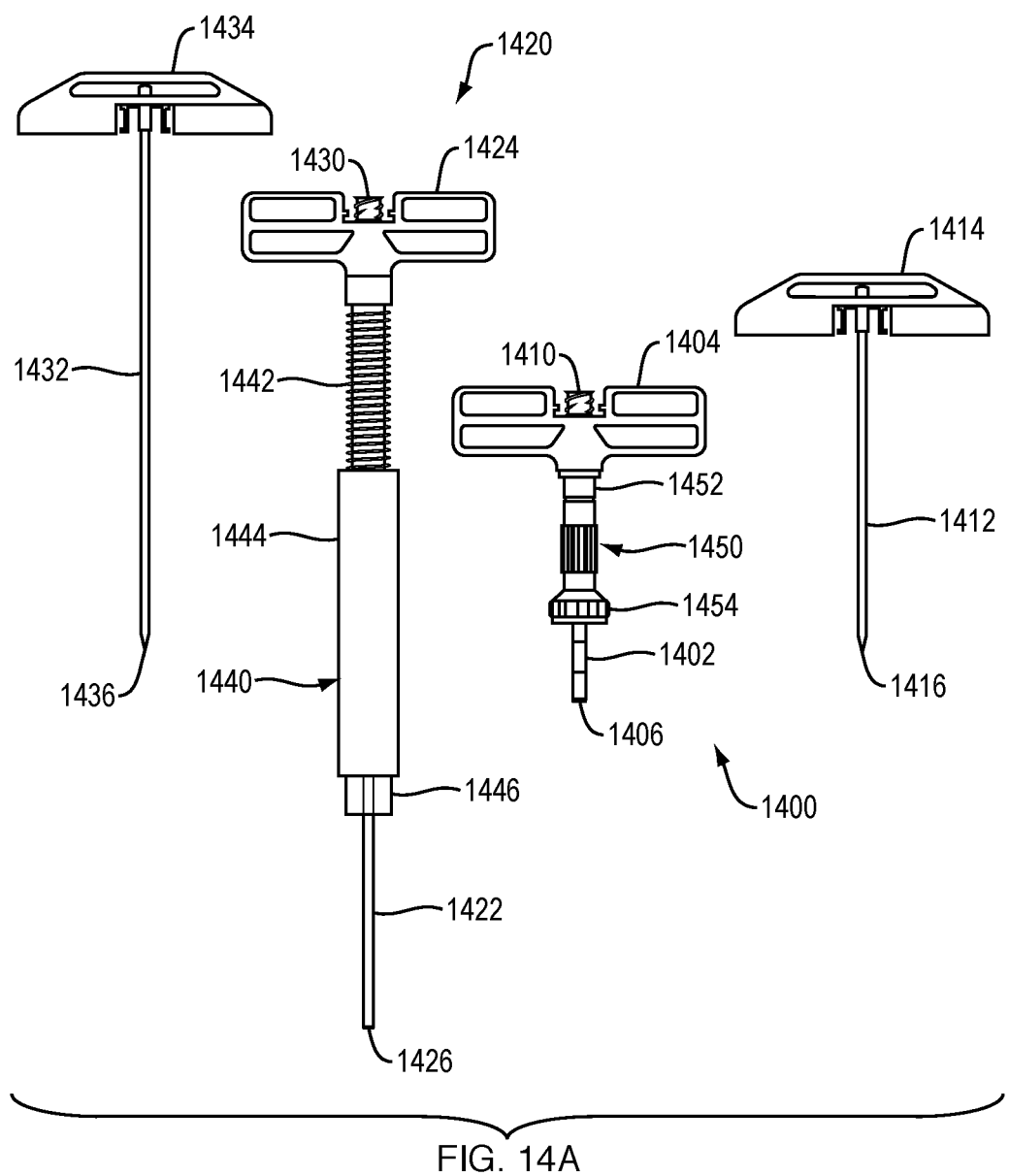
FIG. 14A illustrates another example aspiration device including an aspiration needle, including a screw mechanism, and an introducer needle, including a depth guide.

FIG. 14A illustrates another example aspiration device including an aspiration needle 1420, a locking mechanism 1440 including a screw mechanism, and an introducer needle 1400, including a depth guide 1450.

FIG. 14B illustrates the aspiration needle 1420 and introducer needle 1400 of FIG. 14A with the blunt stylet inserted into the aspiration cannula and the introducer stylet inserted into the introducer cannula.

Locking mechanism 1440 includes a lead screw 1442 in an outer tube 1444 forming a screw advance mechanism to advance the flexible aspiration cannula 1422 into the bone marrow under controlled means. The outer tube 1444 attaches at its distal end to the handle 1404 of the bone marrow needle 1400 via a luer lock connector 1446. Outer tube 1444 is threaded. The threaded tube engages with the threaded guide or lead screw 1442. The flexible aspiration cannula 1422 passes through the outer tube 1444 and through the threaded guide (lead screw) 1442 which is hollow.

In operation, the flexible aspiration needle 1420 is passed into the marrow needle 1400 (rigid cannula) and the outer tube 1444 is locked to the marrow needle via the luer connector 1446. The handle 1424 of the aspiration needle is then turned, e.g., clockwise, to advance the flexible aspiration cannula 1422 into the marrow space. When advanced tot the desired depth, an aspiration syringe is attached to the handle luer fitting 1430. The syringe is aspirated while the entire assembly is slowly withdrawn from the patient by pulling on the handle 1424. The flexible aspiration needle 1420 and marrow needle 1400 thereby withdraw from the patient together.

The advantage of the screw mechanism 1440 is that the flexible aspiration needle 1420 is slowly advanced in the bone marrow in a controlled fashion as compared to advancement with a hammer or pushing motions.

The outer tube 1444 may be made of ABS, polycarbonate (PC) or other rigid polymers. The threaded guide (lead screw) 1442 may be made of stainless steel, polycarbonate (PC) or other rigid polymers. The flexible aspiration cannula 1422 made be made of PEEK, or other suitable materials described herein.

As described, the outer tube 1444 includes a luer lock connector or fitting 1446 at its distal end for coupling to luer lock connector 1410 at the handle of the marrow needle 1400 (rigid cannula). Luer lock connectors or fittings can be securely joined by means of a tabbed hub on the female fitting, e.g., the rigid cannula, which screws into threads in a sleeve on the male fitting, e.g., the outer tube. In addition, luer connectors or fittings feature a taper for making a leak-free connection between a male-taper fitting and its mating female part. Other suitable connectors or fittings may be used to couple and lock the outer tube to the marrow needle (rigid cannula).

An example double needle aspiration system includes the following elements:

An 11 gauge (or 8 gauge) bone marrow aspiration cannula with sharp stylet (introducer needle) and a depth guide;

A 13 gauge (or 11 gauge) bone marrow aspiration cannula with blunt stylet (flexible aspiration needle) and a depth guide; and A 30 ml vacuum lok syringe.

Figure 14C:
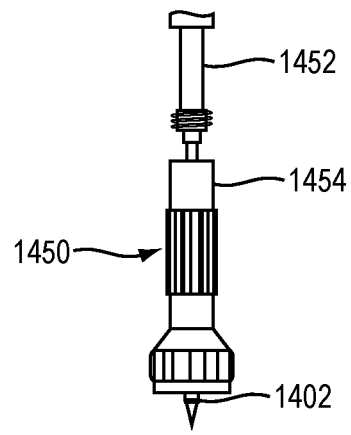
FIG. 14C is a detailed view of the depth guide of FIG. 14A, including the lead screw and threaded tube.

FIG. 14C is a detailed view of the depth guide 1450 of FIG. 14A, including the lead screw 1452 and threaded tube 1452.

Figure 14D:
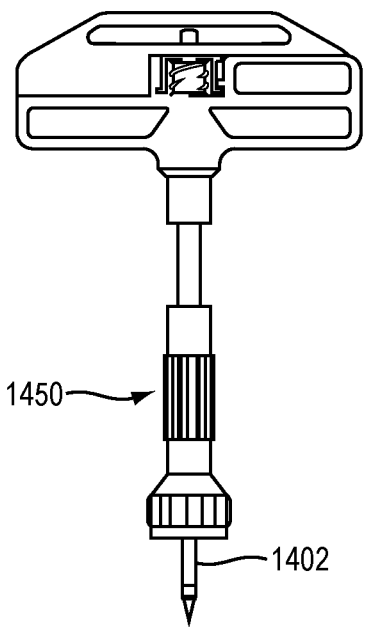
FIG. 14D illustrates the introducer cannula of FIG. 14A with the depth guide in an extended position exposing a short length of the introducer cannula.

FIG. 14D illustrates the introducer cannula 1402 of FIG. 14A with the depth guide 1450 in an extended position exposing a short length of the introducer cannula.

Figure 14E:
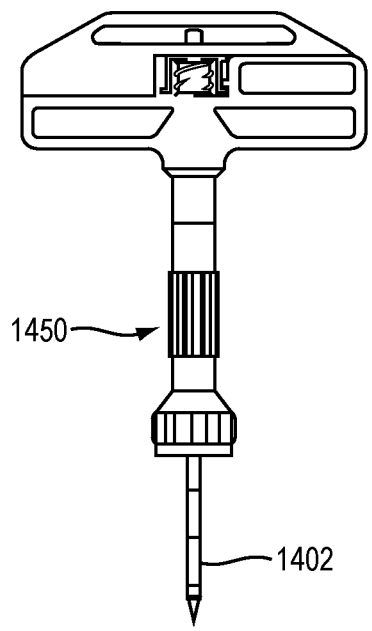
FIG. 14E illustrates the introducer cannula of FIG. 14D with the depth guide in a retracted position exposing a greater length of the introducer cannula.

FIG. 14E illustrates the introducer cannula of FIG. 14D with the depth guide in a retracted position exposing a greater length of the introducer cannula.

The first or introducer cannula 1402 with sharp stylet 1412 is typically short so as to only penetrate the cortical bone and not to penetrate very deep into the trabecular bone. The cannula 1402 can be approximately 3.5-8.0 inches in length preferably about 5 inches in length. The cannula can be 11 gauge in diameter (0.12 inches outer diameter), and can have an adjustable depth guard 1450 (also referred to as a guide, depth guide or depth gauge) that helps control the depth of entry into the bone from, for example, 1 to 8 inches. The needle and stylet fit through a center hole or channel of the depth guard 1450 with the sharp end of the stylet protruding from the distal end. The proximal end of the depth guard 1450 is attached to the handle. The depth guard includes a lead screw 1452 that mates with a threaded tube 1454. Advancing or reversing the lead screw 1452 into the threaded tube 1454 adjusts the amount of exposed cannula 1402 beyond the distal end of the guard 1450. The distance the cannula can travel into the bone space is thus adjusted by the length of the exposed cannual beyond the distal end of the guard. The distal end 1416 of the sharp stylet 1412 is exposed at the distal end of the cannula. Using a twisting motion, the user advances the cannula 1402 through the cortical bone and into the marrow space.

In an example embodiment, the introducer needle 1400 is comprised of a stainless steel cannula 1402 with a molded plastic handle 1404, and a stainless steel stylet 1412 with a molded plastic handle 1414 which mates with the cannula handle 1404 when the stylet 1412 is inserted through the cannula 1402. The introducer needle has a sharpened cannula and stylet that are used to penetrate the outer cortical bone. The adjustable depth guide 1450 coupled to the introducer needle allows the user to adjust the depth to which the needle will advance into the bone space. The length of introducer cannula that extends beyond the distal end of the depth guide represents the furthest distance that the needle can penetrate before being stopped by the depth guide.

Figure 14F:
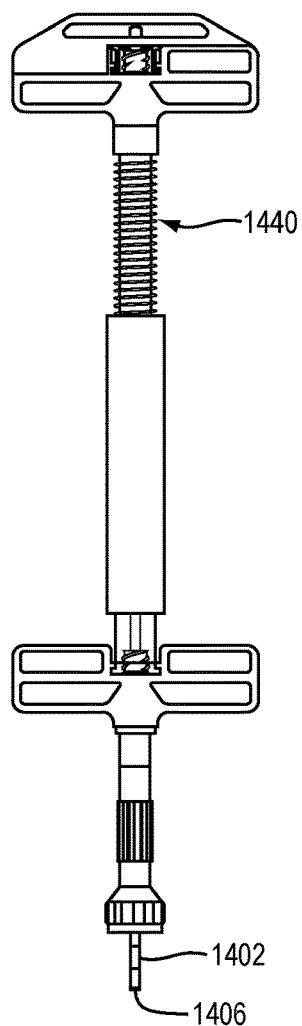
FIG. 14F illustrates the aspiration device of FIG. 14A with the aspiration needle extending through the introducer needle and the screw mechanism in an extended position.

FIG. 14F illustrates the aspiration device of FIG. 14A with the aspiration needle 1420 extending through the introducer needle 1400 and the screw mechanism 1440 in an extended position. As shown, the aspiration cannula does not extend beyond the distal end 1406 of introducer cannula 1402.

Figure 14G:
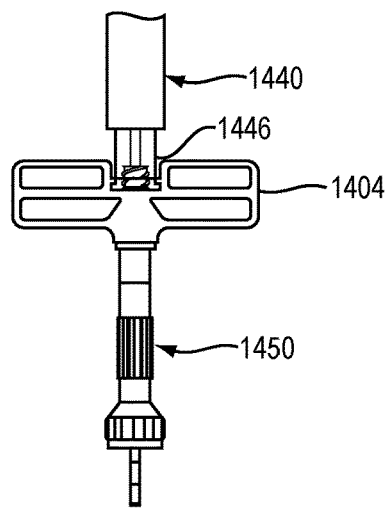
FIG. 14G is a detailed view of the aspiration device of FIG. 14F illustrating the attachment of the aspiration needle to the introducer needle.

FIG. 14G is a detailed view of the aspiration device of FIG. 14F illustrating the attachment of the screw mechanism 1440 of the aspiration needle to handle 1404 of the introducer needle via luer connector 1446.

Figure 14H:
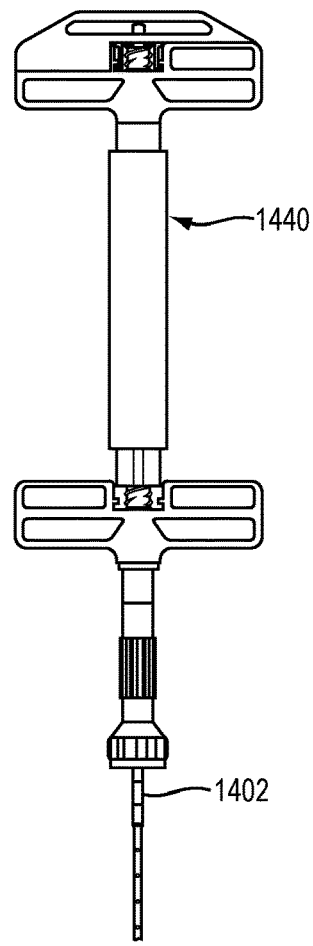
FIG. 14H illustrates the aspiration device of FIG. 14A with the aspiration needle extending through the introducer needle and the screw mechanism in a retracted position.

FIG. 14H illustrates the aspiration device of FIG. 14A with the aspiration cannula 1422 extending through the introducer cannula 1402 and the screw mechanism 1440 in a retracted position.

Figure 14I:
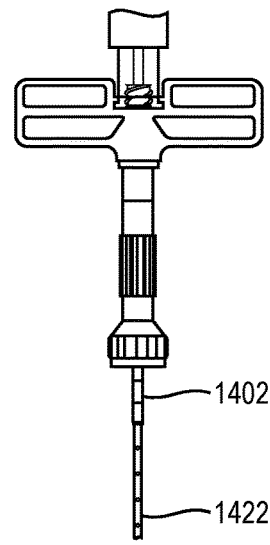
FIG. 14I is a detailed view of the aspiration device of FIG. 14H illustrating the aspiration needle extending beyond the distal end of the introducer needle.

FIG. 14I is a detailed view of the aspiration device of FIG. 14H illustrating the aspiration cannula 1422 extending beyond the distal end of the introducer cannula 1402.

Figure 14J:
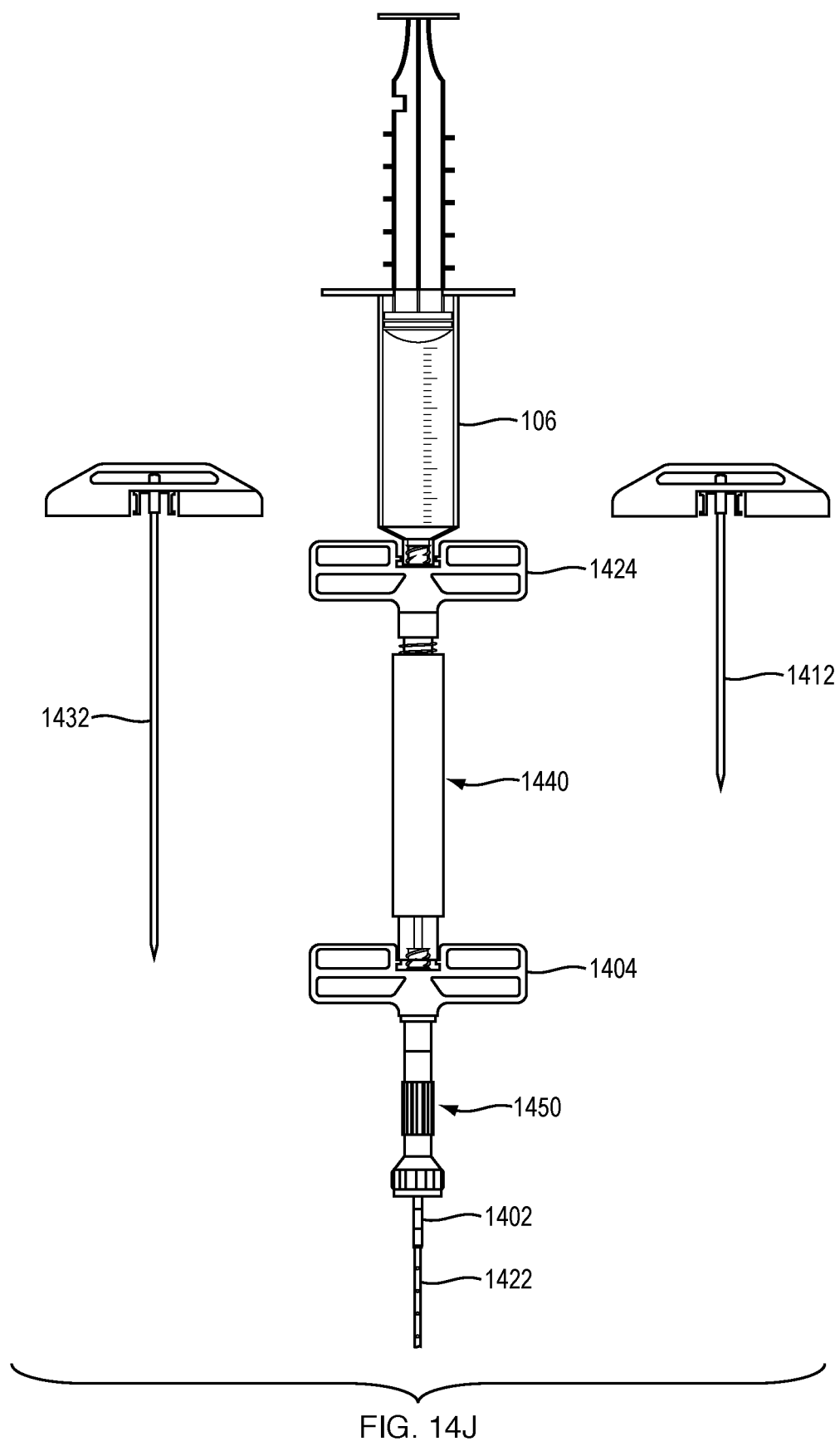
FIG. 14J illustrates the aspiration device of FIG. 14A with the aspiration needle coupled to the introducer needle, the stylets removed and a syringe connected.

FIG. 14J illustrates the aspiration device of FIG. 14A with the aspiration needle 1420 coupled to the introducer needle 1400, the stylets 1412 and 1432 removed, and a syringe 106 connected to the handle 1424 of the aspiration needle.

The flexible aspiration cannula 1422 is typically longer than the introducer cannula 1402, for example by about 1-8 inches, preferably by about 4 inches. In the example shown, the cannula 1422 is 13 gauge in diameter and fits coaxially through the cannula 1402 of the introducer needle, which is a 11 gauge cannula. The flexible aspiration needle also has an adjustable depth guard or guide (screw mechanism 1440) that helps control the depth of entry into the bone. As shown, the aspiration cannula 1422 is closed at the distal (insertion) end and has a blunt tip (see also FIG. 17A). The aspiration cannula and stylet fit through the center hole or channel of the depth guard (screw mechanism 1440) with the distal end of the aspiration cannula protruding from the distal end of the guard (screw mechanism). The proximal end of the depth guard (screw mechanism 1440) is attached to the handle 1424. The depth guard includes a screw mechanism having a lead screw 1442 that mates with a threaded tube 1444. The distal end of the threaded tube has a luer connection. The initial amount of exposed needle beyond the distal end of the depth guard for the second (flexible aspiration) needle is equal to the length of the cannula of the first (introducer) needle. When the stylet of the first needle is removed, the second needle is inserted coaxially into the cannula of the first needle, and the tip of the second needle ends approximately at the distal end of the cannula for the first needle. The depth guard of the second needle attaches to the luer fitting of the handle of the first needle. This is accomplished by connecting the threaded luer connections on the handle of the first needle to the luer connection on the bottom of the threaded tube of the second needle. Twisting the handle in a clockwise direction advances the lead screw into the threaded tube, which in turn adjusts the amount of exposed flexible aspiration needle beyond the distal end of the first 11 gauge needle cannula. The distance the aspiration needle can travel into the bone space, beyond the distance traveled by the introducer cannula, is thus adjusted by the depth guard (screw mechanism 1440) of the aspiration needle. This may be varied, for example, from 0 up to 8 inches.

FIGS. 15A and 15B are respective front and side views of an example introducer needle 1500 including introducer cannula 1502 attached to handle 1504 and introducer stylet 1512 attached to stylet handle 1514. The stylet 1512 extends through introducer handle 1504 and cannula 1502. The stylet 1512 includes a sharp distal tip 1516 that extends beyond the distal end 1506 of introducer cannula 1502. FIG. 15C is a detailed view of the tip 1516 of the introducer stylet 1512 of FIG. 15B.

FIG. 15D is a view of the introducer needle 1500 including a depth guide 1540, which is similar to depth guide 1450 described above in reference to FIG. 14. FIG. 15E is a side view of the introducer cannula of FIG. 15D including a protective sheath 1580 placed over introducer cannula 1502 for packing purposes.

FIGS. 16A-16C are respective side, sectional and perspective views of an example aspiration needle 1600 including a screw mechanism or depth guard 1640. In the example shown, the flexible aspiration needle 1600 includes a stainless steel, blunt closed-end cannula 1622, a molded plastic handle 1624, and a stainless steel stylet with a molded plastic handle 1634 which mates with the cannula handle 1624 when the stylet is inserted through the cannula 1622, as shown. The aspiration needle has a cannula 1622, e.g., a 13 gauge cannula, that has a fenestrated hole pattern (e.g., see FIG. 17A) a closed blunt tip 1626. Aspiration needle can be used to aspirate marrow from the spongy trabecular bone space. Flexibility of the flexible cannula 1622 may be achieved in various ways. For example, the flexible cannula may include reliefs cut into the cannula to adjust flexibility, alternatively, the cannula may be formed from PEEK (polyether ether ketone).

Figure 17A:
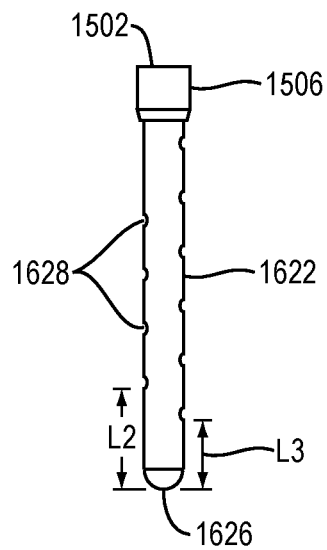
FIGS. 17A-17B are respective front and side views of a distal end of a aspiration cannula including a blunt tip and plural side holes.
Figure 17B:
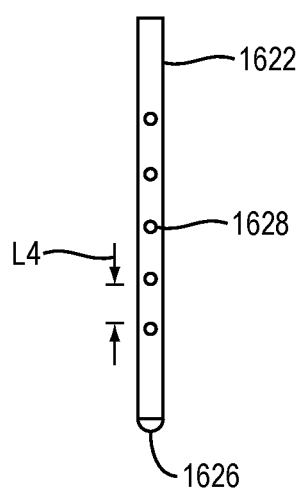

FIGS. 17A-17B are respective front and side views of a distal end of aspiration cannula 1622 including a blunt tip 1626 at the distal end and plural side holes 1628. The aspiration cannula extends through the distal end 1506 of introducer cannula 1502. The aspiration cannula 1622 can contain holes at its distal end, as shown, or along some portion or all of its length. The holes are where marrow is suctioned from. In the example shown, the holes 1628 are arranged in two rows on opposite sides of the aspiration cannula. The holes are evenly spaced in each row by a distance L4, but holes in one row are offset from those of the other row by the difference in lengths L2 and L3. It is contemplated that the hole size can vary so that the pressure created for each hole is approximately the same. Thus holes at the distal end (furthest from the handle) can be larger than holes on the proximal end (closest to the handle). The intent of this is to enable suctioning of marrow evenly along the length of the cannula. Alternatively, the holes may be the same size, as illustrated in FIG. 17B. Alternatively, holes may be only at the distal end of the cannula and marrow is suctioned as the cannula is withdrawn from the patient.

Figure 18A:
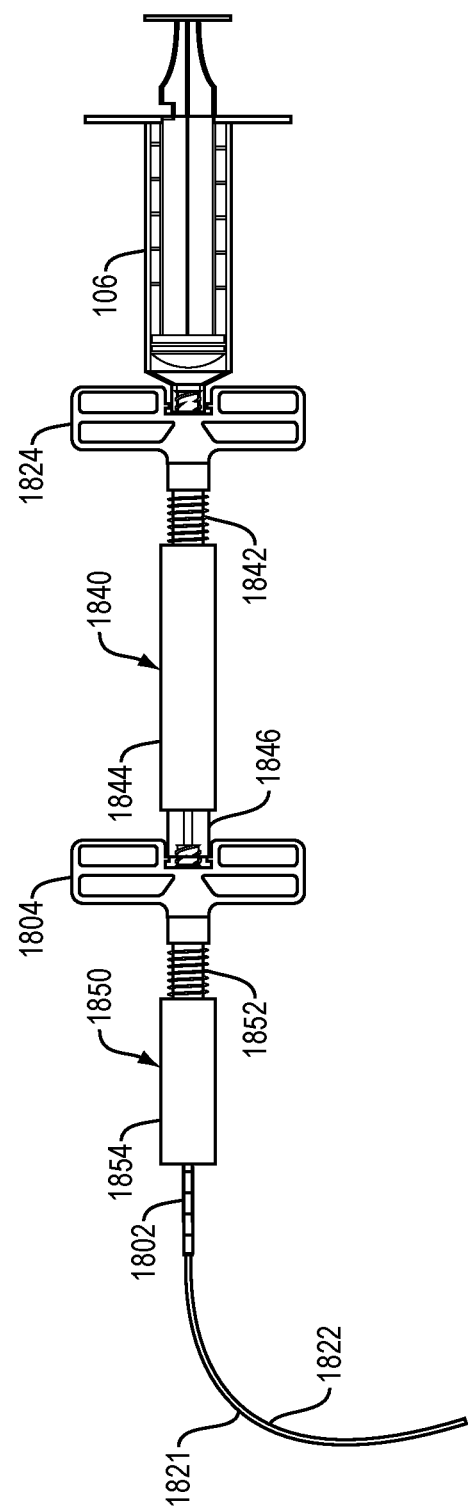
FIG. 18A-18C illustrate an example aspiration devices that includes a wire wound tube.
Figure 18B:
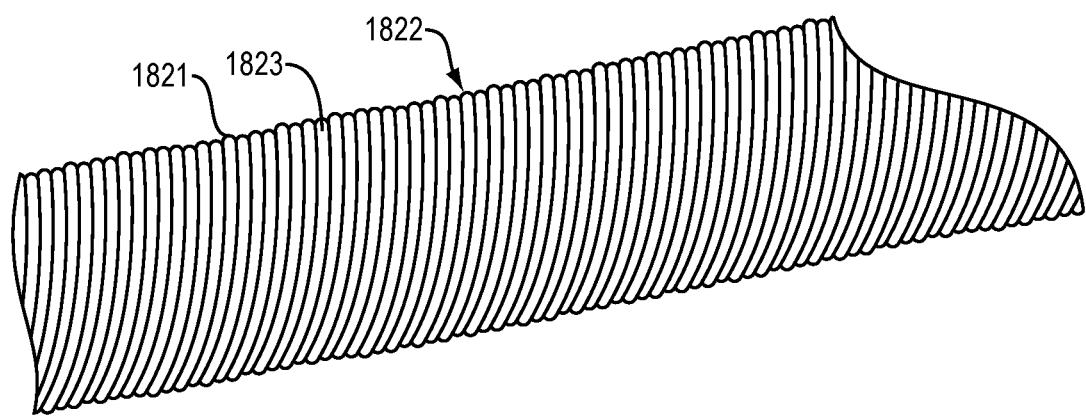
Figure 18C:
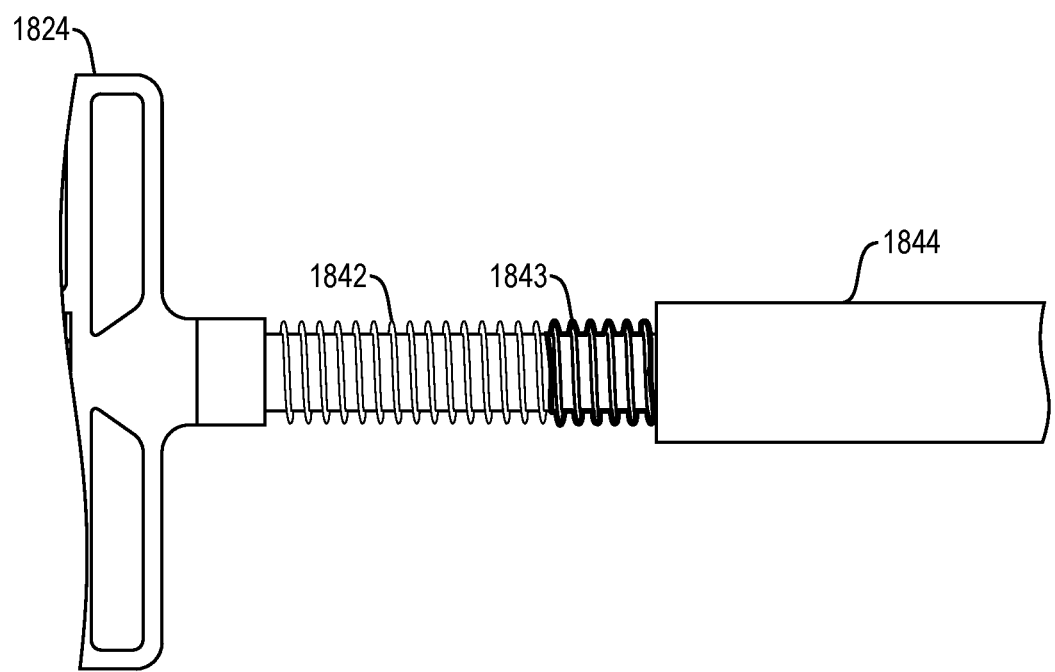

FIG. 18A-18C illustrate an example aspiration devices that includes a wire wound tube 1821 as an aspiration cannula 1822. The entire length of the cannula 1822 may be formed of wire wound tube 1821 or only a portion thereof. For example, a portion of the aspiration cannula 1822, e.g., a proximal portion, may be a solid wall cannula to which a wire wound portion is welded or attached by other suitable means. The aspiration device of FIG. 18A includes an introducer needle including an introducer cannula 1802 attached at its proximal end to an introducer handle 1804. A depth guide 1850, similar to the depth guide described in reference to FIG. 14, is coupled to the handle 1804. The depth guide includes a lead screw 1852 and a threaded tube 1854. As shown, an aspiration needle including aspiration cannula 1822 and handle 1824 is connected to the introducer needle 1804 via luer connector 1846 of screw mechanism 1840. Screw mechanism 1840 includes a threaded receptor 1844, e.g., a threaded tube, and a lead screw 1842, similar to the locking mechanism described in reference to FIG. 14 above. As shown, a syringe 106 can be connected to a luner connector of handle 1824. The device includes air-tight seals at the connection of the lead screw 1842 to the handle 1824, the coupling (threads) of the lead screw to the threaded tube 1844, and at luer connection 1846 to the introducer handle 1804. FIG. 18C illustrates the use of sealing tape 1843 to make the coupling of lead screw 1842 to tube 1844 airtight. FIG. 18B illustrates a detailed view of the wire wound tube of cannula 1822. For example, the outer diameter of the tube can be 0.087 inches, the inner diameter 0.060 inches and the length of the tube can be 13.5 inches. The wire 1823 can be wire part #305V steel, and can be wound in a left hand lay.

The wire wound tube 1821 can have a winding in one direction and the locking mechanism (screw mechanism 1840) can be configured to allow the aspiration cannula 1822 to be withdrawn from the bone marrow by turning the aspiration handle in a direction opposite to direction of the winding, whereby the wire wound tube is tightened as the aspiration cannula is withdrawn.

Embodiments of the bone marrow aspiration device described herein allow for the controlled penetration and aspiration of bone marrow. The bone marrow can be mixed with autograft, synthetic bone and/or allograft bone of the surgeon's choosing prior to the application to a bony defect.

In one example, the bone marrow aspiration device comprises a procedure pack including the following components: two sterile needles with attached guides, and a vacuum syringe 106. Each of the needles are single use and comprised of a stainless steel cannula with a molded plastic handle, and a stainless steel stylet with a molded plastic handle which mates with the cannula handle when the stylet is inserted through the cannula.

Figure 19:
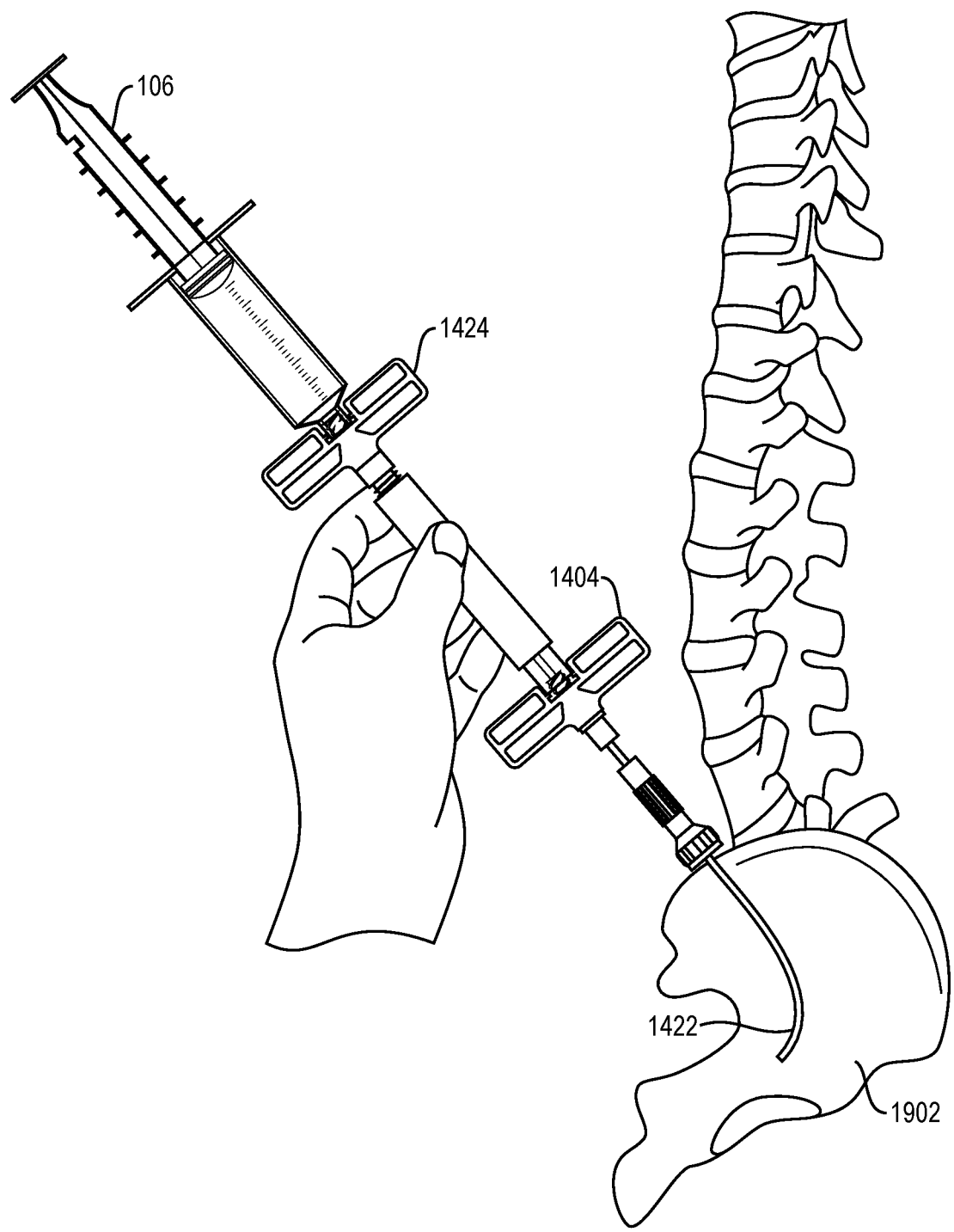
FIG. 19 illustrates insertion of a needle aspiration device into a hip bone.

FIG. 19 illustrates insertion of the aspiration device of FIG. 14J into a hip bone 1902. Starting with the introducer needle 1400, the user adjusts the height of the depth guard 1450 to determine the desired depth which they want the needle to advance. As described above, the introducer needle includes a cannula with a sharp tip and a stylet with a sharp point. After determining the appropriate depth, and while holding the mated handles, the user rotates the introducer needle using a screw-like motion while applying pressure on the bone. The needle bores into the marrow cavity until the guide is against the skin. Once through the bone, the introducer stylet is removed, which exposes a standard luer connection attached to the hollow cannula. The user may at this point attach a syringe to the introducer needle and, applying negative pressure, may aspirate the marrow. Typically, the user then inserts the flexible aspiration needle through the cannula of the introducer needle. The distal end of the depth guide (screw mechanism) on the flexible aspiration needle 1420 has a luer connector that secures the depth guide to the luer hub of the handle of the introducer needle, as described above. At this point the tip of the flexible aspiration needle is inside the cannula of the introducer needle and the depth guard of the flexible aspiration needle is attached to the luer hub of the introducer needle. While holding the mated handles of the flexible aspiration needle with one hand and the bottom end of the depth gauge closest to the handle of the introducer needle, the user twists the needle clockwise while applying downward pressure on the bone. This forces the lead screw of the depth gauge on the flexible aspiration needle 1420 to advance causing its distal end to advance through the trabecular bone. After the flexible aspiration needle 1420 has advanced a sufficient distance as determined by the clinician, the user then removes the blunt stylet, attaches a syringe 106 to the flexible cannula luer hub, and applying negative pressure, aspirates the marrow.

In one example, the entire length of the cannula of the flexible aspiration needle that can penetrate the bone space has a fenestrated hole pattern, as for example describe above in reference to FIG. 16. The negative pressure applied by the clinician allows marrow aspirate to flow through each of these holes. This allows for a broader sampling of marrow. The clinician can rotate the flexible cannula (e.g., by 90° or 180°) to increase the sampling area or region. The clinician can also retract the depth guide while aspirating the marrow by turning the handle of the flexible aspiration needle counter clockwise, to gain an even more diverse sample of marrow aspirate.

Embodiments of double-needle aspiration systems described herein have many advantages. The depth-guard of depth guide of flexible aspiration needle connects to the handle of the introducer needle via a luer connection. The screw mechanism of the depth guard in combination with the luer connection provide for an air-tight fit. This allows the flexible aspiration needle to have holes along its length without risking aspiration of air, something that cannot be done with a traditional aspiration needle. Here, if any holes are not located in bone marrow, those holes are located within the air-tight space of the depth guard. Furthermore, having holes run along a length of the flexible cannula removes the need to withdraw the flexible cannula during aspiration in order to collect bone marrow from a larger area. Advantageously, this can result in a higher count of target cell (e.g., stem cells). One reason for a higher cell count is that there is less dilution of the aspirate with peripheral blood when the aspiration needle (i.e., flexible needle) is not withdrawn during aspiration. With the improved aspiration system described here, one can achieve a higher target cell yield (e.g., cells/ml of aspirate) than using tradition aspiration approaches. The target cell yield with the present system may be comparable to what otherwise can only be achieved through additional cell concentration.

One prototype flexible aspiration needle system was evaluated on the bench in a fresh pig thigh bone. The introducer needle included a depth guide that can adjust the length of introducer needle exposed during the initial entry through the cortical bone. The flexible aspiration needle was inserted through the introducer needle and advanced by threading the handle of the aspiration needle clockwise. The two needles connect by a luer fitting at the introducer handle.

The pig thigh has a very tough cortical bone, a spongy cancellous bone layer and then fat in the middle. In use, the introducer needle was first passed through the cortical bone by manually pushing the needle into the bone or with tapping of a hammer. The depth guide was set so that once the introducer needle passed through the cortical bone, it did not continue further. The introducer cannula was placed at an angle so that the flexible aspiration needle could then be advanced into the bone core.

Once the introducer needle was in place, the flexible aspiration needle was then threaded through it. The aspiration cannula was coupled to the introducer cannula using a screw mechanism, such as the screw mechanism described above in reference to FIGS. 14A-14J. It was easy to feel when the flexible aspiration needle was passing through the cancellous bone, and when it then hit the other side of the bone. It was then possible to continue to advance the flexible aspiration needle by screwing it in until it hit the other side of the bone. Then, one could feel the flexible aspiration needle scraping the bone. The example flexible aspiration needle used was stainless steel and had no aspiration holes drilled into it so it was quite stiff. Even so, during use, it bent so that it followed the bone pathway. When removed, the flexible aspiration needle had taken a permanent set. However, it was still possible to unscrew the flexible aspiration needle and withdraw it through the introducer cannula.

The depth guide allows for controlled entry through the cortical bone. Advancing the flexible aspiration needle with the screwing motion was controlled and allowed the user to feel when the aspiration needle was in cancellous bone or when it is hitting cortical bone. When advancing the flexible aspiration needle, the user needs to hold the depth guide against the bone or the needle assembly may back out. The stainless steel flexible aspiration needle did not include holes in the cannula and tended to be stiff. Including holes in the stainless steel cannula can allow the cannula to bend more. Alternatively, an aspiration cannula made from another material, such as nitinol tubing, may be used.

The bench testing demonstrated that the flexible aspiration needle can be advanced into the trabecular bone space by engaging the screw mechanism (upper depth guide) and screwing the aspiration needle into the bone. The bottom depth guide can serve as a stop to keep the introducer needle from advancing even though there is downward pressure due to the aspiration needle being screwed in downward. This controlled manner of causing the aspiration needle to advance into bone marrow eliminates the need for hammering.

FIG. 20A illustrates an aspiration device, including an introducer cannula 2002, introducer stylet 2012, aspiration cannula 2022, and depth guide 2040, according to an example embodiment of the invention. The depth guide 2040 includes a lead screw 2042 and a threaded tube 2044, similar to the depth guides 1050 and 1450 described in reference to FIGS. 10, 11 and 14. FIG. 20D is a detailed view illustrating the distal end of the introducer cannula 2002 of FIG. 20A. The introducer cannula 2002 includes plural holes 2070. The holes can be near the distal end 2006 of the introducer cannula 2002, for example along one or more sides of the introducer cannula, as shown. FIG. 20B is a detailed view of the distal end of the aspiration cannula 2022 of FIG. 20A. The aspiration cannula 2022 can include a cutout 2072 alignable with at least one of the plural holes of the introducer cannula (see also FIG. 22C). In one example, the distal end of the aspiration cannula is configured to close the opening of the distal end of the introducer cannula (see FIG. 22B). The aspiration needle can include a connector 2046, e.g., a luer connector, to couple to the introducer needle 2004 in an air-tight manner. Thus coupled together, the aspiration needle and introducer needle are moved together by the depth guide. FIG. 20C is a detailed view of the distal end 2016 of the introducer stylet 2012 of FIG. 20A illustrating the sharp tip to penetrate bone.

Figure 21A:
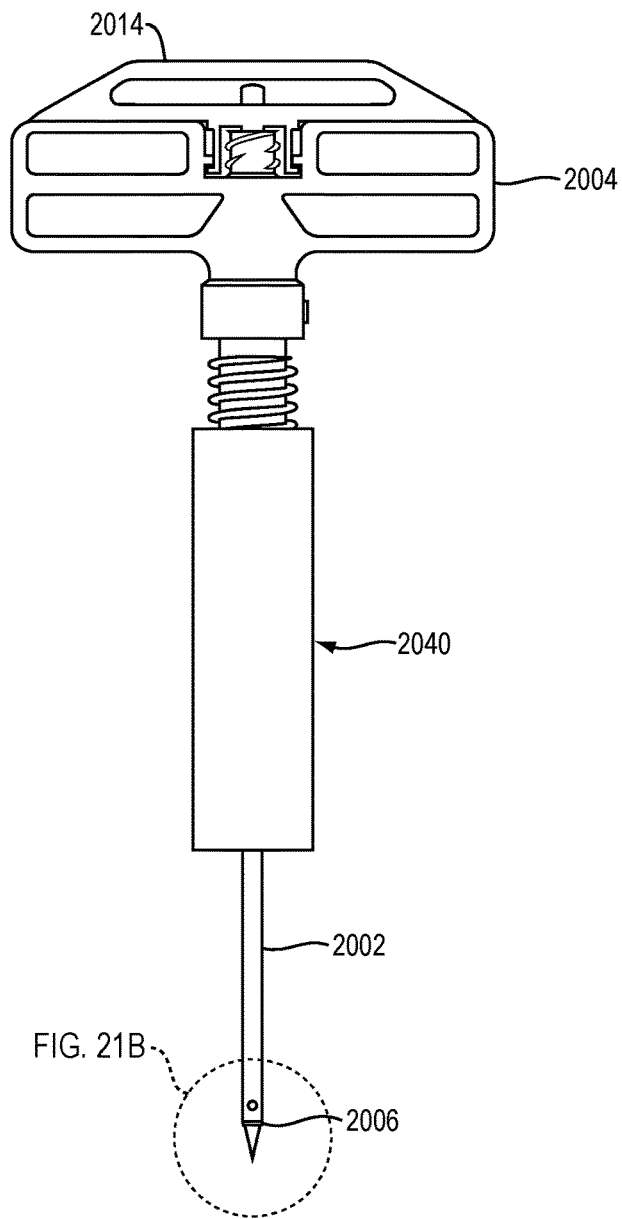
FIG. 21A illustrates the assembled needle including introducer stylet and introducer cannula of FIG. 20A.
Figure 21B:
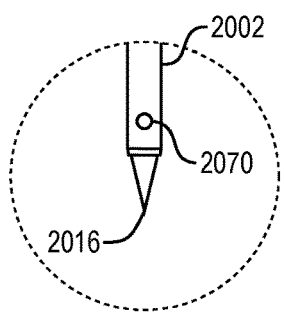
FIG. 21B is a detailed view of the distal end of the introducer needle of FIG. 21A.

FIG. 21A illustrates the assembled needle including introducer stylet 2012 and introducer cannula 2002 of FIG. 20A, including depth guide 2040. FIG. 21B is a detailed view of the distal end 2006 of the introducer needle of FIG. 21A illustrating the sharp tip at the distal end 2016 of introducer stylet.

FIG. 22A illustrates the assembled aspiration device of FIG. 20A with the aspiration cannula inserted through the introducer cannula. FIG. 22B is a detailed view of the distal end of the aspiration device of FIG. 22A illustrating the distal end 2026 of the blunt aspiration cannula closing the distal end of the introducer cannula 2002. FIG. 22C is a sectional view of the distal end of the aspiration device of FIG. 22A illustrating cutout 2072 aligning with at least one of the holes 2070 in cannula 2002.

In the case of marrow aspiration from the iliac crest, if the general procedure performed from a posterior approach such as in spinal fusion (i.e. with the patient lying on side or stomach), accessing the iliac crest is generally not problematic. However, if the surgery is performed from an anterior position such as hip replacement (i.e., patient lying on back), then accessing the iliac crest is more problematic as the bone tends to curve from front to back. Surgeons often flip the patient to gain better access to the bone. The bone marrow aspiration apparatus disclosed herein will allow safe access to the spongy bone from the front, because the shorter introducer needle assembly, such as introducer assembly 200, is not long enough to puncture the other side of the iliac bone. The longer aspiration needle assembly, such as assembly 300, does not have the strength to puncture cortical bone but will travel through marrow. Thus, iliac bone marrow aspirations can be performed when the patient is on his or her back, saving the inconvenience, cost, and additional safety and sterility complications of flipping the sedated patient.

Embodiments of the current invention can be used for bone marrow aspiration to allow a surgeon the ability to 1) access the iliac bone from an anterior position, 2) draw larger volumes of marrow from along the narrow long cavity of the iliac bone, 3) reduce the risk of pushing the needle assembly through the other side of the bone and causing unnecessary trauma, and 4) reduce the number of punctures needed to get a volume of marrow.

A feature of the aspiration needle assembly 300 is that its persistence of length is such that it will not take a sharp turn when initially deployed through the introducer cannula. For example, the stiffness of the combined aspiration needle assembly 300 may be such that for the first quarter inch of travel beyond the distal end of the introducer cannula 202, the aspiration needle assembly will not bend more than 10 degrees with manual force and it will not penetrate cortical bone. The persistence in length of the aspiration cannula may be such that the maximum angle of deflection for the first 0.5 inch segment of the aspiration cannula that extends beyond the distal end of the introducer cannula is between 0 and 30 degrees. The persistence in length prevents the edge of the distal end of the introducer cannula 202, through which the flexible needle assembly 300 is deployed, from shaving off a portion of the outer surface of the flexible aspiration cannula 302 when the aspiration cannula is being pulled back out of the marrow space.

In one embodiment, the stiffness of the stylet, such as stylet 312 of FIG. 3, varies along the length of the stylet. In addition, the diameter of the stylet 312 may vary along the length of the stylet to vary the stiffness of the stylet. For example, the stylet may have a larger diameter near its distal end as compared to mid section of the proximal end of the stylet. The diameter of the stylet, however, may not be larger than the smallest inner diameter of the aspiration cannula 302.

Embodiments of the invention have been described for use in bone marrow aspiration. However, embodiments can be used to aspirate as well as deliver medicine, biologics or other therapy in various tissues. The aspiration device features a double needle assembly. The first or introducer needle assembly, such as assembly 200 of FIG. 2, is stiff enough to make an initial penetration of outer tissue to reach certain targeted subcutaneous tissue. The second, flexible needle assembly, such as assembly 300 of FIG. 3, fits coaxially through the cannula of the first needle assembly.

As for example described above in reference to FIG. 5, the aspiration needle assembly can have a stiffness sufficient to pass through certain less stiff target tissue but does not have the stiffness to penetrate other, stiff tissue surrounding the target tissue. With respect to the aspiration needle assembly 300, it has enough flex and the aspiration cannula is sufficiently lubricious that the stylet 312 can be removed from the cannula 302 even when both are significantly bent.

Besides bone tissue, various other tissues have different stiffness. For example, tendons and ligaments are stiffer than adipose tissue. Clinicians have a need to both deliver and aspirate various fluids. Embodiments of the present invention can be adapted for specific uses. For example the introducer needle assembly 200 can have a stiffness that will penetrate the intra-articular space in a joint. The flexible aspiration needle assembly 300, when deployed through the first needle, can have stiffness such that it will penetrate synovial fluid but not other tissue, such as a ligament tissue. The longer, flexible aspiration needle assembly 300 will not take a set so that it can be easily retrieved through the introducer cannula. Thus the aspiration needle assembly 300 can be used to gain access to a substantial cross section of underlying tissue to deliver therapy through the hollow aspiration cannula with only one external puncture that is made by the introducer needle assembly 200. Another example could be to use the introducer needle assembly to gain access to the femur and use the aspiration needle assembly to travel up the length of the femur to the femoral head. Medication or cells could be delivered through the cannula of the aspiration needle assembly under the femoral head for example, in the treatment of osteonecrosis.

Various materials can be used to make the aspiration needle assembly 300, including the long stylet 312 and aspiration cannula 302. In the case of marrow aspiration, the aspiration needle assembly is preferable be stiff enough to penetrate trabecular bone, including bone marrow, but flexible enough to bend without taking a set, i.e., without kinking or permanently deforming, when it comes into contact with cortical bone. The longer flexible aspiration cannula also needs to be able to bend without taking a set while traveling back along the path created during insertion. If the aspiration cannula collapses, kinks, etc. while being retracted along the path created during insertion, aspiration will not be possible or will be greatly reduced.

The stylet and cannula of the aspiration needle assembly, such as stylet 314 and cannula 302 of FIG. 3, can be made from various materials including plastics, polytetrafluoroethylene (PTFE), polyetheretherketon (PEEK), or metal, including spring steel or shape memory metal. Various prototypes have been made from these different materials. The materials in combination and individually can be selected to have a desired flex and elasticity specific to the particular application. The purpose of the description is not to limit the choice of materials but to give an example of types of material that work. The introducer cannula, such as cannula 202 of FIG. 2, may include any combination of stainless steel, titanium, spring steel, and nickel titanium.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims. It should also be appreciated that the various technical features of the embodiments that have been described may be combined in various ways to produce numerous additional embodiments.

What is claimed is:

1. A method for aspirating bone marrow, the method comprising:

inserting an introducer cannula of an introducer needle into bone, the introducer needle including an introducer handle that is connected to a proximal end of the introducer cannula and a removable stylet that extends through the introducer cannula from the introducer handle, a distal end of the stylet extending beyond a distal, open end of the introducer cannula and including a sharp tip to penetrate bone;

removing the stylet from the introducer cannula;

inserting an aspiration cannula of an aspiration needle into bone marrow through the introducer cannula placed in the bone, the aspiration cannula having a proximal end and a distal end, the proximal end including an opening and the distal end extending beyond the distal end of the introducer cannula, the aspiration needle including an aspiration handle with a luer connection attached to the proximal end of the aspiration cannula;

locking the aspiration cannula to the introducer cannula in a position where the distal end of the aspiration cannula is extending beyond the distal end of the introducer cannula;

aspirating bone marrow through a channel in the aspiration cannula; and moving the introducer cannula from the bone and with the aspiration cannula locked to the introducer cannula, the distal end of the aspiration cannula extending beyond the distal end of the introducer cannula.

2. The method of claim 1, further comprising connecting the introducer handle to the aspiration handle, and wherein moving the introducer cannula includes pulling on the introducer handle to cause the aspiration cannula to be moved with the introducer cannula.

3. The method of claim 1, wherein the aspiration needle includes a blunt stylet having a proximal end and a distal end, the blunt stylet extending through at least a portion of the aspiration cannula from the aspiration handle, and further comprising removing the blunt stylet from the aspiration cannula, the aspiration cannula forming the channel to aspirate bone marrow.

4. The method of claim 1, wherein the aspiration cannula includes a closed, blunt tip at the distal end of the aspiration cannula and at least one side port in fluid communication with the channel in the aspiration cannula, the bone marrow being aspirated though the side port.

5. The method of claim 4, wherein the at least one side port includes plural side ports arranged along a length of the aspiration cannula near the distal end of the aspiration cannula.

6. The method of claim 1, wherein the bone marrow is aspirated during retrieval of the aspiration cannula from the bone.

7. The method of claim 1, further comprising coupling the aspiration cannula to the introducer cannula in an air-tight manner.

* * * * *